(12) United States Patent
Wolf et al.

(10) Patent No.: US 9,140,640 B2
(45) Date of Patent: Sep. 22, 2015

(54) METHOD FOR IDENTIFYING LAYERS PROVIDING CORROSION PROTECTION IN CRUDE OIL FRACTIONS

(71) Applicants: H. Alan Wolf, Morris Plains, NJ (US); Fang Cao, Annandale, NJ (US); Saul C. Blum, Monroe, NJ (US); Alan M. Schilowitz, Highland Park, NJ (US); Shiun Ling, Washington, NJ (US); James E. McLaughlin, Oakton, VA (US); Srdan Nesic, Athens, OH (US); Peng Jin, Athens, OH (US); Gheorghe Bota, Athens, OH (US)

(72) Inventors: H. Alan Wolf, Morris Plains, NJ (US); Fang Cao, Annandale, NJ (US); Saul C. Blum, Monroe, NJ (US); Alan M. Schilowitz, Highland Park, NJ (US); Shiun Ling, Washington, NJ (US); James E. McLaughlin, Oakton, VA (US); Srdan Nesic, Athens, OH (US); Peng Jin, Athens, OH (US); Gheorghe Bota, Athens, OH (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 191 days.

(21) Appl. No.: 14/070,835

(22) Filed: Nov. 4, 2013

(65) Prior Publication Data

US 2014/0134743 A1    May 15, 2014

Related U.S. Application Data

(60) Provisional application No. 61/722,911, filed on Nov. 6, 2012.

(51) Int. Cl.
*G01N 17/00* (2006.01)
*C23C 26/00* (2006.01)
*C10G 7/10* (2006.01)
*G01N 23/20* (2006.01)
*G01N 23/225* (2006.01)

(Continued)

(52) U.S. Cl.
CPC ............... *G01N 17/006* (2013.01); *C10G 7/10* (2013.01); *C10G 9/16* (2013.01); *C10G 9/203* (2013.01); *C23C 26/00* (2013.01); *G01N 17/043* (2013.01); *G01N 23/20* (2013.01); *G01N 23/2252* (2013.01)

(58) Field of Classification Search
CPC ..................................................... G01N 17/00
USPC .............................................................. 436/6
See application file for complete search history.

(56) References Cited

U.S. PATENT DOCUMENTS 5,630,964 A * 5/1997 Babaian-Kibala et al. ........................ 252/389.23
5,869,195 A * 2/1999 Ramanarayanan et al. .. 428/610

(Continued)

OTHER PUBLICATIONS

The International Search Report and Written Opinion of PCT/US2013/068234 dated Feb. 5, 2014.

(Continued)

*Primary Examiner* — Arlen Soderquist
(74) *Attorney, Agent, or Firm* — Glenn T. Barrett; Andrew T. Ward

(57) ABSTRACT

A method for determining and identifying corrosion protective layers that provide corrosion protection against crude oils and crude oil fractions is disclosed. The method identifies naturally occurring constituents in crude oils that indirectly provide corrosion protection. A method assessing the potential of these constituents is also disclosed. The method includes exposing metal coupons with the crude oil or crude fraction of interest at the expected operating temperature of concern. The corrosion potential assessment further analyzes the exposed coupons with transmission electron microscopy and an additional high temperature exposure that challenges the tenacity of the protection offered by the corrosion protective layer.

14 Claims, 19 Drawing Sheets

(51) Int. Cl.
  *G01N 17/04* (2006.01)
  *C10G 9/16* (2006.01)
  *C10G 9/20* (2006.01)

(56) References Cited

U.S. PATENT DOCUMENTS

| | | | | |
|---|---|---|---|---|
| 6,022,494 | A * | 2/2000 | Sartori et al. | 252/387 |
| 6,294,387 | B1 * | 9/2001 | Yepez et al. | 436/6 |
| 8,118,994 | B2 | 2/2012 | Messer et al. | |
| 2004/0107769 | A1 * | 6/2004 | Blum et al. | 73/86 |
| 2006/0063263 | A1 * | 3/2006 | Yeganeh et al. | 436/6 |
| 2006/0091044 | A1 * | 5/2006 | Lehrer et al. | 208/47 |
| 2007/0119747 | A1 * | 5/2007 | Harrell et al. | 208/47 |
| 2008/0164137 | A1 * | 7/2008 | Messer et al. | 203/3 |
| 2010/0116718 | A1 * | 5/2010 | Subramaniyam | 208/348 |
| 2010/0126842 | A1 * | 5/2010 | Subramaniyam | 203/7 |
| 2010/0147739 | A1 * | 6/2010 | Levine et al. | 208/14 |
| 2010/0264064 | A1 * | 10/2010 | Mahesh | 208/47 |
| 2011/0066388 | A1 * | 3/2011 | Snelling et al. | 702/30 |
| 2011/0160405 | A1 * | 6/2011 | Subramaniyam | 525/333.7 |
| 2011/0214980 | A1 * | 9/2011 | Subramaniyam | 203/7 |
| 2012/0045361 | A1 * | 2/2012 | Subramaniyam | 422/12 |
| 2013/0289320 | A1 * | 10/2013 | Barney et al. | 585/3 |

OTHER PUBLICATIONS

Hau et al., "Predicting Sulfidic and Naphthenic Acid Corrosion," Corrosion, Dec. 2009, vol. 65, No. 12, pp. 831-844.

Wu et al., "Study on high-temperature naphthenic acid corrosion and erosion-corrosion of aluminized carbon steel," Journal of Materials Science, 2004, vol. 39, pp. 975-985.

Qu et al., "Erosion-corrosion of Q235 and 5Cr1/2Mo steels in oil with naphthenic acid and/or sulfur compound at high temperature," Materials and Corrosion, 2005, vol. 56, No. 8, pp. 533-541.

S.G. Kapusta, A. Ooms, A. Smith, F. van den Berg and W. Fort, "Safe Processing of Acid Crudes", NACE Corrosion 2004, Paper No. 04637.

W.A. Derungs, Naphthenic Acid Corrosion—An Old Enemy of the Petroleum Industry, Corr., 1956, 12, 617-622.

J. Gutzeit, "Naphthenic Acid Corrosion in Oil Refineries", Mater. Perform., 1977, 16, 24-35.

R.L. Piehl, Naphthenic acid corrosion in crude distillation units, Mater. Perform., 1988, 27 (1), 37-43.

E. Slavcheva, B. Shone and A. Turnbull, "Review of Naphthenic Acid Corrosion in Oil Refining", Br. Corr. J., 1999, 34 (2), 125-131.

R.D. Kane and M.S. Cayard, "Understanding Critical Factors that Influence Refinery Crude Corrosiveness", Mater. Perform., 1999, 48-54.

O. Yepez, "Influence of Different Sulfur Compounds on Corrosion due to Naphthenic Acid", Fuel, 2005, 84, 97-104.

J.L. Hau, O. Yepez, M.I. Specht and R. Lorenzo, "The Iron Powder Test for Naphthenic Acid Corrosion Studies," Corr. Paper No. 379, 1999, 1-16.

J.L. Hau, O. Yepez, L. Torres and M.I. Specht, "Classifying Crude Oils According to Corrosivity Using the Fe Powder Test", Corr. Paper No. 00699, 2000, 1-9.

H.L. Craig, "Naphthenic Acid Corrosion in the Refinery", Corrosion 95, NACE Annual Conference, Paper No. 333.

G.M Bota, D. Qu, S. Nesic, H.A. Wolf, "Naphthenic Acid Corrosion of Mild Steel in the Presence of Sulfide Scales Formed in Crude Oil Fractions at High Temperature", Corr. Paper No. 10353, 2010, 1-20.

R.D. Kane and M.S. Cayard, "A Comprehensive Study on Naphthenic Acid Corrosion", NACE 2002, Paper No. 02555.

J. Hau, "Predicting Sulfidic and Naphthenic Acid Corrosion", Corrosion, 65, 2009, 831-844.

H.D. Dettman, N. Li, D, Wickramasinghe and J. Luo, "The Influence of Naphthenic Acid and Sulphur Compound Structure on Global Crude Corrosivity Under Vacuum Distillation Condition", NACE 2010 Northern Area Western Conference, Feb. 15-18, Calgary, Alberta, Canada.

M.P. Barrow, L.A. McDonnell, X. Feng, J. Walker and P.J. Derrick, "Determination of the Nature of Naphthenic Acids Present in Crude Oils Using Nanospray Fourier Transform Ion Cyclotron Resonance Mass Spectrometry: The Continued Battle Against Corrosion", Anal. Chem., 75, 2003, 860-866.

K.R. Lewis, M.L. Daane and R. Schelling, Nace Corrosion 1999, Paper 377.

B.S. Huang, W.F. Yin, D.H. Sang and Z.Y. Jiang, "Synergy effect of naphthenic acid corrosion and sulfur corrosion in crude oil distillation unit", Applied Surface Science, 259, 2012, 664-670.

H. Tamura, "The role of rusts in corrosion and corrosion protection of iron and steel", Corrosion Science, 50, 2008, 1872-1883.

D. de la Fuente, I. Diaz, J. Simancas, B. Chico and M. Morcillo, "Long-term atmospheric corrosion of mild steel", Corrosion Science, 53, 2011, 604-617.

E. McCafferty, "Oxide Networks, Graph Theory, and the Passivity of Fe—Cr—Ni Ternary Alloys", Journal of the Electrochemical Society, 154 (10), 2007, C571-C578.

S. Giddey, B. Cherry, F. Lawson and M. Forsyth, "Stability of oxide films formed on mild steel in turbulent flow conditions of alkaline solutions at elevated temperatures", Corrosion Science, 43, 2011, 1497-1517.

J. Chen, K. Huang and S. Liu, "Hydrothermal preparation of a protective Fe3O4 film on Fe foil", Corrosion Science, 50, 2008, 1982-1986.

B. Garcia, A. Lamzoudi, F. Pillier, H. Nguyen Thi Le and C. Deslouis., "Oxide/Polypyrrole Composite Films for Corrosion Protection of Iron", Journal of the Electrochemical Society, 149 (12), 2002, 5560-5566.

A.N. Mansour and C.A. Melendres, Study of the Structure and the Morphology of Oxide Films on Amorphous Al—Fe—Ce Alloys by XPS and SEM, Electrochem. Soc., vol. 142, No. 6, Jun. 1995.

H.J. Grabke, "Oxidation of NiAl and FeAl", Intermetallics, 7, 1999, 1153-1158.

A. Zahs, M. Spiegel and H.J. Grabke, "The influence of alloying elements on the chlorine-induced high temperature corrosion of Fe—Cr alloys in oxidizing atmospheres", Materials and Corrosion, 1999, 50, 561-578.

Hou, "Beyond the Sulfur Effect", Oxidation of Metals, vol. 52, Nos. 3/4, 1999.

D.J. Baxter and K. Natesan, "Breakdown of Chromium Oxide Scales in Sulfur-Containing Environments at Elevated Temperatures", Oxidation of Metals, vol. 31, Nos. 3/4, 1989.

A. Hernandez-Espejel, M.A. Dominguez-Crespo, R. Cabrera-Sierra, C. Rodrigues-Meneses and E.M. Arce-Estrada, "Investigations of corrosion films formed on API-X52 pipeline steel in acid sour media", Corrosion Science, 52, 2010, 2258-2267.

F. Carrette, M.C. Lafont, G. Chatainier, L. Guinard and B. Pieraggi., Analysis and TEM examination of corrosion layers grown on Alloy 690 exposed to pressurized water at 325 deg. C, Surf. Interface Anal., 2002, 34, 135-138.

M. Da Cunha Belo, M. Walls, N.E. Hakiki, J. Corset, F. Picquenard, G. Sagon and D. Noel, "Composition, Structure and Properties of the Oxide Films Formed on the Stainless Steel 316L in a Primary Type PWR Environment", Corrosion Scmm, 1998, vol. 40, No. 2/3, 447-463.

Y. Tanaka, M. Nakai, T. Alahori, M. Niinomi, Y. Tsutsumi, H. Doi and T. Hanawa, Characterization of air-formed surface oxide film on Ti—29Nb—13Ta—4.6Zr alloy surface using XPS and AES, Corrosion Science, 50, 2008, 2111-2116.

X. Peng, "Nanoscale assembly of high-temperature oxidation-resistant nanocomposites", Nanoscale, 2010, 262-268.

H. Kim, N. Hara and K. Sugimoto., "Dependence of Corrosion Resistance of Fe2O3—Cr2O3 Artificial Passivation Films on Crystal Structure and Chemical State of Constituent Elements of the Films", Journal of the Electrochemical Society, 1999, 146 (10), 3679-3685.

I. Diez-Perez, F. Sanz and P. Gorostiza, "In situ studies of metal passive films", Current Opinion in Solid State and Materials Science, 10, 2006, 144-152.

M.T. Greiner, M. Festin and P. Kruse, "investigation of corrosion-inhibiting aniline oligomer thin films on iron using photoelectron spectroscopy", J. Phys. Chem., 2008, 18991-19004.

(56) References Cited

OTHER PUBLICATIONS

S. Mischler, A. Spiegel and D. Landolt, "The role of passive oxide films on the degradation of steel in tribocorrosion systems", Wear, vols. 225-229, Part 2, Apr. 1999, 1078-1087.

V.K. Pareek, T.A, Ramanarayanan, J.D. Mumford, A. Ozekcin and J.C. Scanlon, "The Role of Morphology and Structure in the Kinetic Evolution of Iron-Sultide Films on Fe-Base Alloys", Oxidation of Metals, vol. 41, Nos. 5/6, 1994.

V.K. Pareek, A. Ozekcin, J.D. Mumford and T.A. Ramanarayanan, "Transport of sulfur through preformed spinel films on low alloy Fe—Cr steels", Journal of Materials Science Letters, 16, 1997, 128-130.

W. Kai, D.L. Douglass and F. Gesmundo, "The corrosion of Fe—Mo Alloys in H2/H20/H2S atmospheres", Oxidation of Metals, vol. 37, Nos. 5/6, 1992.

N.K. Das, T. Shoji and Y. Takeda, "Fundamental study of Fe—Cr binary alloy oxide film interfaces at 288 deg. C by computational chemistry calculations", Corrosion Science, 52, 2010, 2349-2352.

M. El Kamel, A. Galtayries, P. Vermaue, B. Albinet, G. Foulonneau, X. Roumeau, B. Roncin and P. Marcus, "Sulfidation kinetics of industrial steels in a refinery crude oil at 300 deg. C reactivity at the nanometer scale", Surf. Interface Anal., 2010, 42, 605-609.

W.T. Bakker, "Variables affecting mixed oxidant corrosion of stainless steels in gasifiers", materials and Corrosion, 51, 2000, 219-223.

A. Ul-Hamid "TEM Study of the Effect of Y on the Scale Microstructures of Cr2O3- and Al2O3-Forming Alloys", Oxidation of Metals, vol. 58, Nos. 1/2, Aug. 2002.

E. Schumann, J.C. Yang, M. Ruhle and M.J. Graham, "High-Resolution SIMS and Analytical TEM Evaluation of Alumina Scales on B—NiAl Containina Zr or Y", Oxidation of Metals, vol. 46, Nos. 1/2, 1996.

J. Fukushima, K. Kodaira and T. Matsushita., "Preparation and Formation Process of Various Iron Oxide Films by Thermal Decomposition of Iron Naphthenate", Yogyo Kyokai Shi, 84/11, 1978, 529-533.

N.R. Smart, A.P. Rance and A.M. Pritchard, "Laboratory Investigation of Naphthenic Acid Corrosion under Flowing Conditions", NACE Corrosion 2002, Paper No. 0248, 1-23.

J. Mayer, L.A. Giannuzzi, T. Kamino and J. Michael, "TEM Sample Preparation and FIB-Induced Damage", Materials Research Bulletin, vol. 32, 2007.

\* cited by examiner

Example 1 – Oil – Tufflo, TAN – 1.75mgKOH/g; Sulfur - None

Example 2 – Oil – Tufflo, TAN – 1.75mgKOH/g; Sulfur – 0.25 wt%

Example 3 – Oil – Tufflo, TAN – none; Sulfur – 0.25 wt%

Example 1 – Oil – Tufflo, TAN – 1.75mgKOH/g; Sulfur - None

Example 4 – Oil – Fraction G, TAN – 4.9mgKOH/g; Sulfur – 0.15 wt%

Example 4 – Oil – Fraction G, TAN – 4.9mgKOH/g; Sulfur – 0.15wt%

Example 5 – Oil – Fraction A, TAN – 1.7mgKOH/g ; Sulfur – 0.51wt%

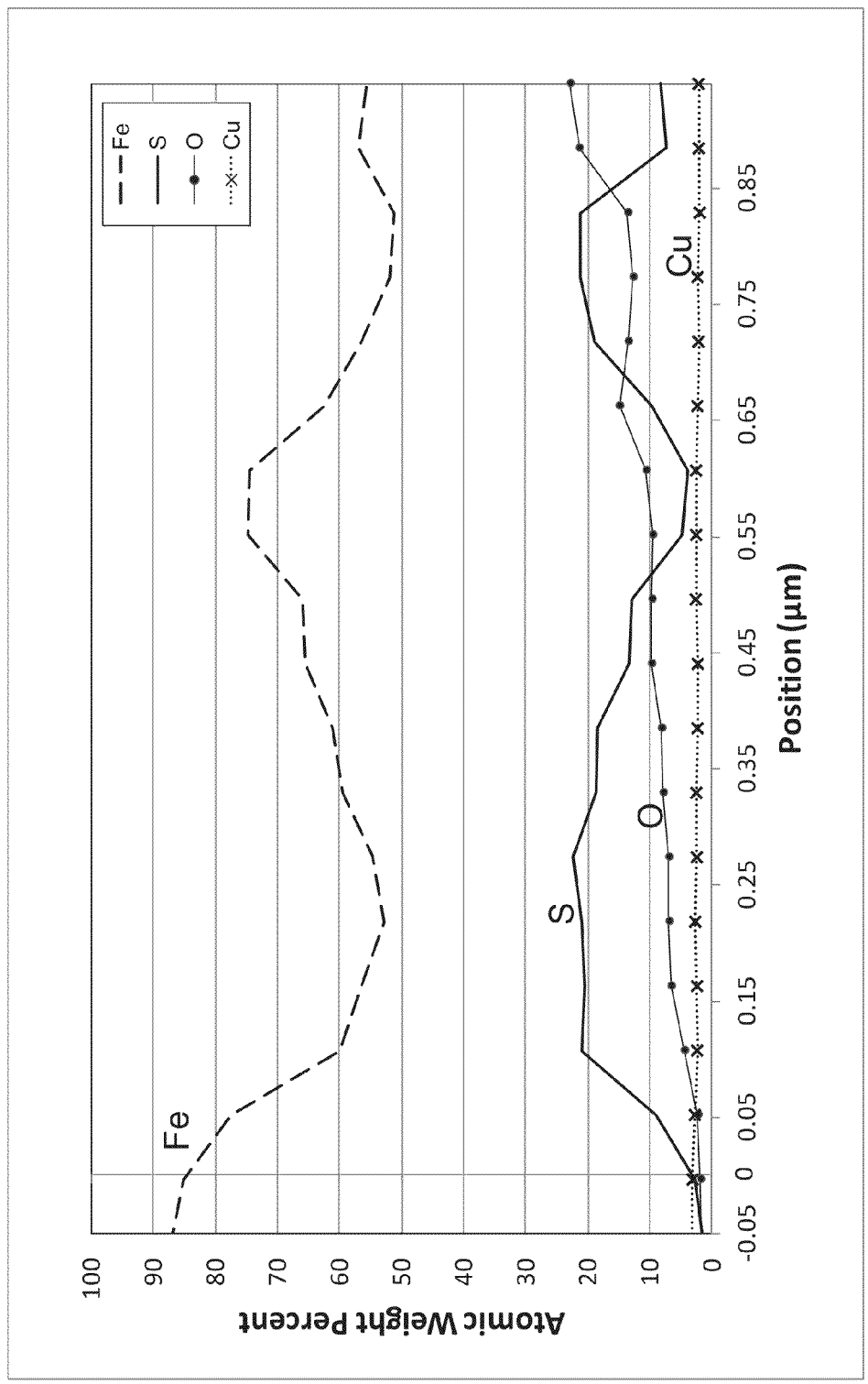

Example 7 – Oil – Fraction B, TAN – 0.1mgKOH/g; Sulfur – 1.9 wt%

METHOD FOR IDENTIFYING LAYERS PROVIDING CORROSION PROTECTION IN CRUDE OIL FRACTIONS

FIELD OF THE INVENTION

The presently disclosed subject matter generally relates to a method for determining and identifying corrosion protective layers that provide corrosion protection against crude oils or fractions thereof. The presently disclosed subject matter identifies naturally occurring constituents in crude oils that indirectly contribute to and enhance corrosion protection against crude oils and provides a method to assess the potential of the same.

DESCRIPTION OF RELATED ART

Corrosion is a significant problem in petroleum refineries and other industrial plants that process corrosive materials. Corrosion can cause deterioration of valves, gauges and other equipment. Corrosion can also cause leaks with large environmental and financial costs. All of these may result in downtime for repairs and replacement of refinery components. Heavy and acidic crude oils can be particularly corrosive.

Increasing oil prices and limited availability of light sweet crudes on oil markets sparked a new interest for processing these heavy and acidic crude oils in spite of the disadvantages of processing such crude oils. Well known for their high acidic and sulfur content, heavy crude oils may have considerable corrosive effects at high temperatures. The acidity is predominately due to naphthenic acids measured as Total Acid Number (TAN). TAN is expressed as mg KOH/gram of oil using ASTM D664). Oil extraction, transport, and its processing in refineries raises a multitude of challenges for the industry, that can be expressed in economic costs and benefits. Reducing production costs entices oil companies to process "opportunity crudes"—low quality corrosive crude oils with high naphthenic acid and sulfur contents that are less costly than the so called "sweet crudes", the former of which are readily available on the oil market. Processing of these acidic crudes at high temperatures in refineries forced the refinery engineers to adopt special strategies for mitigating their corrosive effects. These strategies included blending crudes, inhibitor additives, changes to inspection monitoring, adjustment to process parameters, and/or selecting better materials for various critical refinery components (see Kapusta, "Safe Processing of Acid Crudes," NACE Corrosion 2004, Paper No. 637). Kapusta describes the benefits of corrosion protection and also outlines the economic incentives for optimizing the refining of high naphthenic acid crude oils.

Part of the strategy for identifying better materials requires a better understanding the mechanism of naphthenic acid corrosion and its interaction with sulfidic corrosion. Naphthenic acid corrosion was first identified in refineries in the 1920s (see Derungs, "Naphthenic Acid Corrosion—An Old Enemy of the Petroleum Industry,"Corr. 1956, 12, 617-622). Further research studies described the naphthenic acid corrosion process in a more comprehensive manner and gave the first model of naphthenic corrosion. (see Gutzeit, "Naphthenic Acid Corrosion in Oil Refineries," Mater. Perform., 1977, 16, 24-35 and Piehl, "Naphthenic acid corrosion in crude distillation units," Mater. Perform. 1988, 27 (1), 37-43) The empirical model was based on case studies and laboratory tests and was used as a basic reference for naphthenic acid corrosion rate predictions in refineries.

These early classical models of naphthenic acid corrosion had limitations on accuracy because certain specific highly acidic crudes that were processed have proven not to be as corrosive as the model predicted (see Slavcheva et al., "Review of Naphthenic Acid Corrosion in Oil Refining," Br. Corr. J. 1999, 34 (2), 125-131). Efforts were made to investigate other important factors in predicting corrosion like the interaction with sulfur compounds, naphthenic acid molecular weight and structure, etc. Engineers currently use different methods for predicting sulfidation and naphthenic acid corrosion rates in refineries. The most common models are McConomy curves and iso-corrosion curves (see Kane et al., "Understanding Critical Factors that Influence Refinery Crude Corrosiveness," Mater. Perform. 1999, July, 48-54). Both methods predict corrosion rates related to oil sulfur content. The "iron powder test" assesses corrosion based on the interactions between naphthenic acids and sulfur compounds (see Yépez, "Influence of Different Sulfur Compounds on Corrosion due to Naphthenic Acid", Fuel, 2005, 84, 97-104; and Hau et al., "The Iron Powder Test for Naphthenic Acid Corrosion Studies", Corr. Paper No. 379., 1999, 1-16; Hau et al., "Classifying Crude Oils According to Corrosivity Using The Fe Powder Test", Corr. Paper No. 00699, 2000, 1-9). These methods were based on empirical observation of real cases and laboratory tests and did not take into consideration any physical aspects and phenomena that evolved on the metal surface during corrosion protective layer formation and acidic attack.

Craig discloses a formulation to quantify the protective nature of the iron sulfide layer formed at the metal surface (see Craig, "Naphthenic Acid Corrosion in the Refinery," Corrosion 95, NACE Annual Conference, Paper Number 333). This formulation of the "naphthenic acid corrosion index" (NACI) is a ratio of corrosion rate compared to the weight of the iron sulfide layer. The underlying assumption for this formulation is that an increase in the mass per unit area of the layer provided more protection from naphthenic acid corrosion. A lower NACI result suggests that sulfur corrosion dominates over naphthenic acid corrosion. The empirical nature of NACI has been unable to accurately predict the corrosion aggressiveness of a crude fraction. For example, lower values of NACI, caused by higher concentrations of reactive sulfur species should directionally lead to the formation of more layers. No correlation between layer mass and naphthenic acid corrosion protection has been shown (see Bota et al., "Naphthenic Acid Corrosion of Mild Steel in the Presence of Sulfide Scales Formed in Crude Oil Fractions at High Temperature," Corr. Paper No. 10353, 2010, 1-20).

It is already known from practical refinery experience that when "opportunity crudes" are processed, the naphthenic acid corrosion and sulfur corrosion occur together mainly in distilling towers, their side streams, and their adjacent transfer lines. The two corrosive groups (i.e. naphthenic acids and sulfur compounds) influence each other and their effect cannot be simply separated. Both are very reactive at high temperatures. Naphthenic acid is particularly aggressive at high flow velocity encountered in refinery transfer lines (see Kane, R. D. et. al, "A Comprehensive Study on Naphthenic Acid Corrosion," NACE 2002, Paper No. 555). Sulfur and naphthenic acid have been identified as the major contributors to corrosion in refinery crude units. The operating temperature range for these refinery units is typically 200-440° C.

Notwithstanding the vast historical studies that have been conducted to assess the corrosivity of crude oil and their fractions, the available corrosion models are still unable to accurately predict relative or absolute corrosivity. (see "Refining Industry Naphthenic Acid Corrosion", NACE Corrosion Information Series). The primary complications of formulating reliable predictive models relate to 1) the interaction of the naphthenic acid corrosion component with sulfidation corrosion, and 2) establishing a universal model based only on acid and sulfur concentrations. Corrosivity is not reliably translated to an arbitrary crude slate with the same sulfur and acid concentrations (see Hau, J. "Predicting Sulfidic and Naphthenic Acid Corrosion," Corrosion 65 (2009), 831-844). Input to these models includes process conditions such as temperature, flow, pressure, and metallurgy composition. Typically, the model input describing the crude fraction includes some measure of sulfur and naphthenic acid concentration. Some models may also incorporate naphthenic acid and sulfur speciation. U.S. Pat. No. 8,118,994 discloses naphthenic acids with different corrosive properties. Even with these enhancements, the model reliability is not good.

More recently, both the boiling point of the naphthenic acid and the available sulfur species were considered as part of the corrosion assessment process (see Dettman et. al, "The Influence of Naphthenic Acid and Sulphur Compound Structure on Global Crude Corrosivity Under Vacuum Distillation Condition," NACE 2010 Northern Area Western Conference, February 15-18, Calgary, Alberta, Canada). The findings demonstrate that even when these parameters are assessed, the actual corrosivity of the crude vacuum distillate cannot be predicted reliably. One factor contributing to this prediction inconsistency was attributed to the formation of a sulfide film at the metal surface. It was suggested that the differences in the corrosion protection offered by the film could be linked to the thermal history of the crude. The use of negative ion mode nanospray Fourier transform ion cyclotron resonance (FTICR) mass spectrometry for speciation of the naphthenic acid has also been proposed as a means to improve the ability to predict the corrosivity of the acid (see Barrow, M. P. et. al, "Determination of the Nature of Naphthenic Acids Present in Crude Oils Using Nanospray Fourier Transform Ion Cyclotron Resonance Mass Spectrometry: The Continued Battle Against Corrosion," Anal. Chem. 75 (2003) 860-866).

The discrepancies of classical crude oil corrosion modeling could be attributed to a protective layer formed on the metal surface. It has been reported that the protective layer is iron sulfide (see Lewis et al., NACE Corrosion 1999, Paper No. 377). Existing models did not properly account for the corrosion protection provided by the iron sulfide layer. The experimental methodology demonstrated that naphthenic acid corrosion could be mitigated when the steel was previously exposed for a specified time and at a specified temperature with some crude fractions. Not all crude fractions provide the same degree of corrosion protection. There was no correlation with the naphthenic acid and sulfur concentration and the corrosion protection. Bota et al. disclose an assessment of the iron sulfide layer by means of scanning electron microscope (SEM) and energy dispersive x-ray spectroscopy (EDS). SEM and EDS provide a means to measure layer composition and layer morphology with a resolution of a few microns. Bota et al concluded that there was no discernable correlation between the layer composition and morphology and the corrosion protection.

The availability of the sulfide film to suppress naphthenic acid corrosion has more recently been examined (see Huang, B. S. et. al, "Synergy effect of naphthenic acid corrosion and sulfur corrosion in crude oil distillation unit," Applied Surface Science 259 (2012), 664-670). Coupling corrosion measurements with SEM, EDS, and XRD (x-ray diffraction), it was concluded that the $Cr_5 S_8$ that formed at the surface of 316 stainless steel was the enabler that provided enhanced corrosion resistance compared to a Q235 carbon-manganese steel (with no chromium). In some cases, the XRD analyses also showed the presence of iron oxide, $Fe_3O_4$ which was attributed the presence of oxygen in the reaction kettle. The iron oxide was not attributed to providing corrosion protection.

Some have shown that oxide layers have the ability to provide corrosion protection in some environments, and the oxide layer providing corrosion protection is related to atmospheric or aqueous environments. Once this passivation layer forms, it may retard the metal from undergoing continued oxidation. This principle is the basis for "weathering" steels in air where the formation of a rust layer inhibits additional corrosion in low alloy steels (see Tamura, "The role of rusts in corrosion and corrosion protection of iron and steel," Corrosion Science 50 (2008) 1872-1883; and de la Fuente et al, "Long-term atmospheric corrosion of mild steel," Corrosion Science 53 (2011) 604-617). Different methods are available for the formation of the protective oxide layer typically in the form of FeOOH, $Fe_2O_3$, $Fe_3O_4$. Models have been proposed (Oxide Networks, Graph Theory, and the Passivity of Fe—Cr—Ni Ternary Alloys, E. McCafferty, Journal of The Electrochemical Society, 154 (10) C571-0578 (2007)) relating the structure of the oxide compound to the passivity it affords for corrosion protection.

In addition to the application of oxide films (layers) to inhibit atmospheric corrosion, similar benefits are also applicable to aqueous corrosion. Protection for sodium hydroxide corrosion has been demonstrated. (see Giddey et al., "Stability of oxide films formed on mild steel in turbulent flow conditions of alkaline solutions at elevated temperatures," Corrosion Science 43 (2001), 1497-1517). Protection for mildly acid corrosion has also been demonstrated for mild steel (see Chen et al., "Hydrothermal preparation of a protective $Fe_3O_4$ film on Fe foil," Corrosion Science 50 (2008) 1982-1986). Giddey illustrates a more compact layer having more stability in turbulent environments. Both Giddey and Chen attribute the passivation to the formation of $Fe_3O_4$ (magnetite). Giddey and Chen use different methods for the passivation processes. Garcia discloses improving the corrosion resistance for iron by forming a $Fe_3O_4$ passivation layer by using oxide particles in suspension during the electrodeposition process (see Garcia et al., "Oxide/Polypyrrole Composite Films for Corrosion Protection of Iron," Journal of The Electrochemical Society, 149(12), B560-B566, 2002). Similarly, Mansour shows the benefits of oxide layers for corrosion protection in aqueous environments for aluminum-based alloys (see Mansour et al., "Study of the Structure and the Morphology of Oxide Films on Amorphous Al—Fe—Ce Alloys by XPS and SEM," Electrochem. Soc., Vol. 142, No. 6, June 1995). Grabke (Oxidation of NiAl and FeAl, Intermetallics 7 (1999) 1153-1158), Zahs et al. ("The influence of alloying elements on the chlorine-induced high temperature corrosion of Fe—Cr alloys in oxidizing atmospheres",), and Hou ("Beyond the Sulfur Effect," Oxidation of Metals, Vol. 52, Nos. 3/4, 1999) disclose aluminum oxide layers formed at 1000° C. on materials alloyed with Cr, Y, Ce and which should provide layers for corrosion protection. However, not all conditions are favorable to form a protective layer. In particular, Hou and also Baxter ("Breakdown of Chromium Oxide Scales in Sulfur-Containing Environments at Elevated Temperatures", Baxter et al., Oxidation of Metals, Vol. 31, Nos. 3/4, 1989) disclose the effect of sulfur in the alloy and the layer. Although the sulfur-free alloys are generally considered beneficial in forming a protective layer, the alloying elements also play a significant role. Hernández-Espejel et al. ("Investigations of corrosion films formed on API-X52 pipeline steel in acid sour media", Corrosion Science 52 (2010)

2258-2267) discloses the role of oxide layers with iron sulfide in aqueous sour, ambient temperature environments on API-X52 steel (non-alloyed). Corrosion performance was poorly correlated with linear polarization and electrical impedance spectroscopy. SEM images detailing morphology and composition also provided little differentiation with respect to corrosion.

Carrette ("Analysis and TEM examination of corrosion layers grown on Alloy 690 exposed to pressurized water at 325° C., (Carrette et al., Surf. Interface Anal. 2002; 34: 135-138) reported on the morphopology and composition of oxide layers formed at 325° C. (high pressure water) on Alloy 690 (a high Cr—Ni alloy). De Cunha Belo et al ("Composition, Structure, and Properties of the Oxide Films Formed on the Stainless Steel 316L in a Primary Type PWR Envirnonment," Corrosion Scmm, Vol. 40, No. 2/3, pp. 447-463, 1998) conducted tests in a similar environment on 316L stainless steel that focused on characterizing steel and identified an innermost layer of chromium-rich oxide. Although the environment, chemistry, and metallurgy are variable, these works illustrate the difficulty to correlate layer details with corrosion protection.

Atmospheric corrosion passivation at ambient temperature by surface oxide films on steels alloyed with Ti, 29Nb, Ta, Zr has been demonstrated. (see Tanaka et al., "Characterization of air-formed surface oxide film on Ti-29Nb-13Ta-4.6Zr alloy surface using XPS and AES," Corrosion Science 50 (2008) 2111-2116). More recently, nano-materials are being developed that are designed to promote the formation of a protective oxide layer (see "Nanoscale assembly of high-temperature oxidation-resistant nanocomposites, Nanoscale, X, Peng, Nanoscale, 2010, 2, 262-268).

Kim examined the crystalline structure of iron oxide and chrome oxide layers on platinum (see Kim et al., "Dependence of Corrosion Resistance of $Fe_2O_3$—$Cr_2O_3$ Artificial Passivation Films on Crystal Structure and Chemical State of Constituent Elements of the Films," Journal of The Electrochemical Society, 146 (10) 3679-3685 (1999)). Layers were deposited in the temperature range of 150° C.-350° C. using a vapor deposition technique. Subsequently, aqueous corrosion tests were made using HCl. Various correlations were established between corrosion resistance, layer formation temperature, and crystalline vs. amorphous morphology.

Diez-Perez discloses a number of new in-situ methods for analyzing the properties of passive layers on metals (see Di ez-Pé rez et al., "In situ studies of metal passive films," Current Opinion in Solid State and Materials Science 10 (2006) 144-152). However, these methods are primarily applicable for electrochemical situations rather than the hydrocarbon environment of a refinery crude unit. Greiner describes the application of photoelectron emission spectromicroscopy for the study of passive oxide layers (see Greiner et al., "Investigation of Corrosion-Inhibiting Aniline Oligomer Thin Films on Iron Using Photoelectron Spectroscopy," J. Phys. Chem. C 2008, 112, 18991-19004). Although these results yield considerable information regarding the electrochemical nature of the layers, no correlation to corrosion resistance is identified. Passive oxide layers have also provided beneficial wear protection for metal surfaces subject to friction (see Mischler et al., "The role of passive oxide films on the degradation of steel in tribocorrosion systems," Wear, Volumes 225-229, Part 2, April 1999, Pages 1078-1087).

Pre-formed oxide layers at on 4130 steel (chromoly steel with Cr <1%) have been evaluated. The beneficial reduction of sulfidation was attributed to reduced diffusivity through the oxide film (see Pareek et al., "The Role of Morphology and Structure in the Kinetic Evolution of Iron-Sulfide Films on Fe-Base Alloys," Oxidation of Metals, Vol. 41, Nos. 5/6, 1994; and Pareek et al., "Transport of sulfur through pre-formed spinel films on low alloy Fe—Cr steels," Journal of Materials Science Letters, 16 (1997) 128-130). This benefit was preferentially observed at 260° C. rather than at 540° C. The reduced benefit at 540° C. was attributed to the observation that the layer did not provide complete coverage of the metal surface. Oxide layers fail to form above 600° C. in $H_2/H_2O/H_2S$ environments on Fe—Mo alloys (see Kai et al., "The Corrosion of Fe—Mo Alloys in $H_2/H_2O/H_2S$ Atmospheres," Oxidation of Metals, Vol. 37, Nos. 5/6, 1992). The quantum chemical molecular dynamics method can also evaluate oxygen diffusivity through oxide layers (see Das et al., "Fundamental study of Fe—Cr binary alloy-oxide film interfaces at 288° C. by computational chemistry calculations," Corrosion Science 52 (2010) 2349-2352). The findings demonstrate that the presence of Cr in the layer ($Cr_2O_3$) is beneficial in this regard compared to $Fe_2O_3$. Autoclave tests conducted at 300° C. exposing carbon steel, 5-Cr steel, and a 304 stainless steel to a high sulfur crude oil illustrate the formation of an iron sulfide layer on the carbon and 5-Cr steels (see El Kamel et al., "Sulfidation kinetics of industrial steels in a refinery crude oil at 300° C.: reactivity at the nanometer scale," Surf Interface Anal. 2010, 42, 605-609) conducted. In contrast, the formation of a $Cr_2O_3$ layer on the stainless steel was attributed to improving the resistance to sulfidation corrosion. Bakker (Variables affecting mixed oxidant corrosion of stainless steels in gasifiers, Materials and Corrosion 51, 219-223 (2000)) evaluated the oxide passivation protection on stainless steels from HCl, $H_2S$, and chlorides.

Ul-Hamid discloses an improvement to layer adherence and corrosion protection performance for Ni—Cr steels by alloying with rare earth metals (see Ul-Hamid, "TEM Study of the Effect of Y on the Scale Microstructures of $Cr_2O_3$— and $Al_2O_3$-Forming Alloys," *Oxidation of Metals*, Vol. 58, Nos. 1/2, August 2002). Similar findings are reported by Schumann et al., "High-Resolution SIMS and Analytical TEM Evaluation of Alumina Scales on p-NiAl Containing Zr or Y" Oxidation of Metals, Vol. 46, Nos. 1/2, 1996, which discloses the use of high-resolution secondary ion mass spectrometry (SIMS) and an analytical TEM for an analysis of the oxide layer.

The prior art describes formation of oxides where air and/or water are the oxygen sources. However, none of the prior art discloses the forming an oxide passivation layer in either the absence of air or in a non-aqueous environment (e.g. petroleum) protective for naphthenic acid corrosion but where the source of oxygen is from the naphthenic acid itself. Fukushima discloses that in the presence of air, iron naphthenate can decompose to $Fe_2O_3$ or $Fe_3O_4$ on a glass substrate (see Fukushima et al., "Preparation and Formation Process of Various Iron Oxide Films by Thermal Decomposition of Iron Naphthenate," Yogyo Kyokai Shi, 84/11, 1976, 529-533). $Fe_2O_3$ is preferentially formed at temperatures higher than 400° C. Lower temperature enables the formation of $Fe_3O_4$. The existence of magnetite and minor amount of hematite and pyrrhotite has been found on carbon steel surface after experimentation with a high-TAN (2.9 mgKOH/g) crude (see Smart et al., Laboratory Investigation of Naphthenic Acid Corrosion Under Flowing Conditions. *NACE Corrosion* 2002 Paper 02484, 1-23). The findings dismissed the role of naphthenic acid in forming a protective film since tests with pure oil and naphthenic acid failed to form an observable scale based on weight loss. The layer was suspected to be protective, and was attributed to the available sulfur and other crude oil components.

SUMMARY OF INVENTION

The presently disclosed subject matter describes a method for determining the propensity of a crude oil or crude oil fraction to form a spinel-type (e.g. $Fe_3O_4$ or $FeCr_2O_4$ and may include sulfur) oxide corrosion protective layer or layer that provides protection from subsequent naphthenic acid corrosion.

The method includes exposing metal coupons to the subject fluid under specified temperature conditions. The exposed coupons provide a means to directly measure the corrosion protection provided by the crude oil exposure process and examine the morphology and composition (chemical and phase) of the corrosion protective layer near the metal surface. The coupon and associated deposition are examined using transmission electron microscopy (TEM). TEM analysis provides corrosion protective layer morphology information and elemental composition of the corrosion protective layer near the metal surface with nanometer resolution using energy dispersive x-ray spectroscopy (EDS). In addition to TEM and EDS, the methodology includes the use of x-ray diffraction (XRD) to examine the corrosion protective layer phase composition as a means to detect and distinguish between spinel-type oxides (e.g. $Fe_3O_4$, magnetite) vs. other oxides (e.g. $Fe_2O_3$, hematite). The protective nature of the layer is related to its phase composition, chemical composition including the presence of oxygen at the metal/layer interface, and its layered structure.

Without intending to limit the applicability to various metals, the presently disclosed subject matter is applicable to carbon steels, such as ASTM A106 pipe or ASTM A516 plate and low chromium steels, as described by ASTM A387 and ASTM SA-335. The formation of an iron sulfide or an iron-chromium-sulfide corrosion protective layer on these steels has been observed and has been linked to providing corrosion protection from naphthenic acid. The presently disclosed subject matter enabled with TEM submicron resolution technology and supplemented by XRD, demonstrates that the corrosion protection relates to the submicron oxygen-containing layer identified as spinel-types such as magnetite ($Fe_3O_4$) and chromite ($FeCr_2O_4$) for carbon steels and chrome steels, respectively. Demonstration is achieved through explicit corrosion testing. The close proximity of the oxygen to the steel surface and the presence of chromium are important parameters that enable assessment of the layers' protection to naphthenic acid corrosion. The source of the oxygen is the naphthenic acid. These oxide-types form via the decomposition of naphthenic acid or via the decomposition of metal naphthenates formed following initial attack of the metal by these acids. This is especially useful in applications such as refinery crude units which operate without oxygen in the process stream.

The presently disclosed subject matter is directed to a method for evaluating the degree of corrosion protection provided by the corrosion protective layer formed on a metal surface from exposure to a corrosive fluid. The metal surface is made from steel. The steel is either a Cr-enriched steel and/or a carbon steel. The method includes selecting a fluid containing naphthenic acids. The fluid is a crude oil or a crude oil fraction. The fluid has a TAN measurement of at least 0.5 mgKOH/g and contains no more than 4% sulfur by weight. The metal surface is pre-treated by exposing the metal surface to the fluid for a predetermined time period and a predetermined temperature to form a corrosion product layer thereon. The predetermined time period is in the range of 16-48 hours. The predetermined temperature is approximately between 200° C. and 440° C. The pre-treating of the metal surface is performed at an autogenous pressure consistent with the process. Pre-treatment is conducted in commercially available reactors such as a Parr 4250. The method further includes identifying the corrosion protection degree by the corrosion product layer adjacent to the metal surface by examining the morphology and chemical composition of the layer adjacent to the metal surface to confirm the formation of spinel-type oxide layer at the metal surface. Examining the morphology and chemical composition includes using transmission electron microscopy. The elemental composition data are obtained using energy dispersive X-ray spectroscopy. The method further includes examining the corrosion protective layer phase composition using x-ray diffraction analysis. The method may further include assessing the corrosion protection potential of the corrosion protective layer. Assessing the correction protection potential may include measuring the pre-treatment weight loss of the metal surface, "challenging" the corrosion protective layer formed on the metal surface by exposing the layer to a known corrosive fluid, measuring the weight loss of the metal sample after challenging the layer, and comparing the pre-treatment weight loss and the weight loss after challenging the layer.

The presently disclosed subject matter is also directed to a method of providing corrosion protection for a metal surface. The metal surface is formed made from steel. The steel is preferably one of a Cr-enriched steel and/or a carbon steel. The metal surface is part of a component in a refinery. The method includes selecting a fluid containing naphthenic acid, wherein the fluid has a TAN measurement of at least 0.5 mgKOH/g and no more than 4% sulfur by weight. The fluid is preferably one of a crude oil or a crude oil fraction. The method further includes exposing the metal surface to the fluid for a predetermined time at a predetermined temperature. The predetermined time period is in the range of 16-48 hours. The predetermined temperature is approximately between 200° C. and 440° C. The autogenous pressure is consistent with anticipated process conditions. The method further includes forming a protective layer on the metal surface.

BRIEF DESCRIPTION OF THE DRAWINGS

FIG. 2A shows the relative elemental composition of the corrosion protective layer on 5-Cr steel using EDS while

FIG. 3A shows the relative elemental composition of the corrosion protective layer on 5-Cr steel using EDS while

FIG. 4A shows the relative elemental composition of the corrosion protective layer on 5-Cr steel using EDS while

FIG. 5A shows the relative elemental composition of the post challenge corrosion protective layer on 5-Cr steel using EDS while

FIG. 6A shows the relative elemental composition of the corrosion protective layer on 5-Cr steel using EDS while

FIG. 7A shows the relative elemental composition of the corrosion protective layer on carbon steel using EDS while

FIG. 8A shows the relative elemental composition of the corrosion protective layer on 5-Cr steel using EDS while

FIG. 9A shows the relative elemental composition of the corrosion protective layer on carbon steel using EDS while

FIG. 10A shows the relative elemental composition of the corrosion protective layer on 5-Cr steel using EDS while

DETAILED DESCRIPTION

Figure 1:
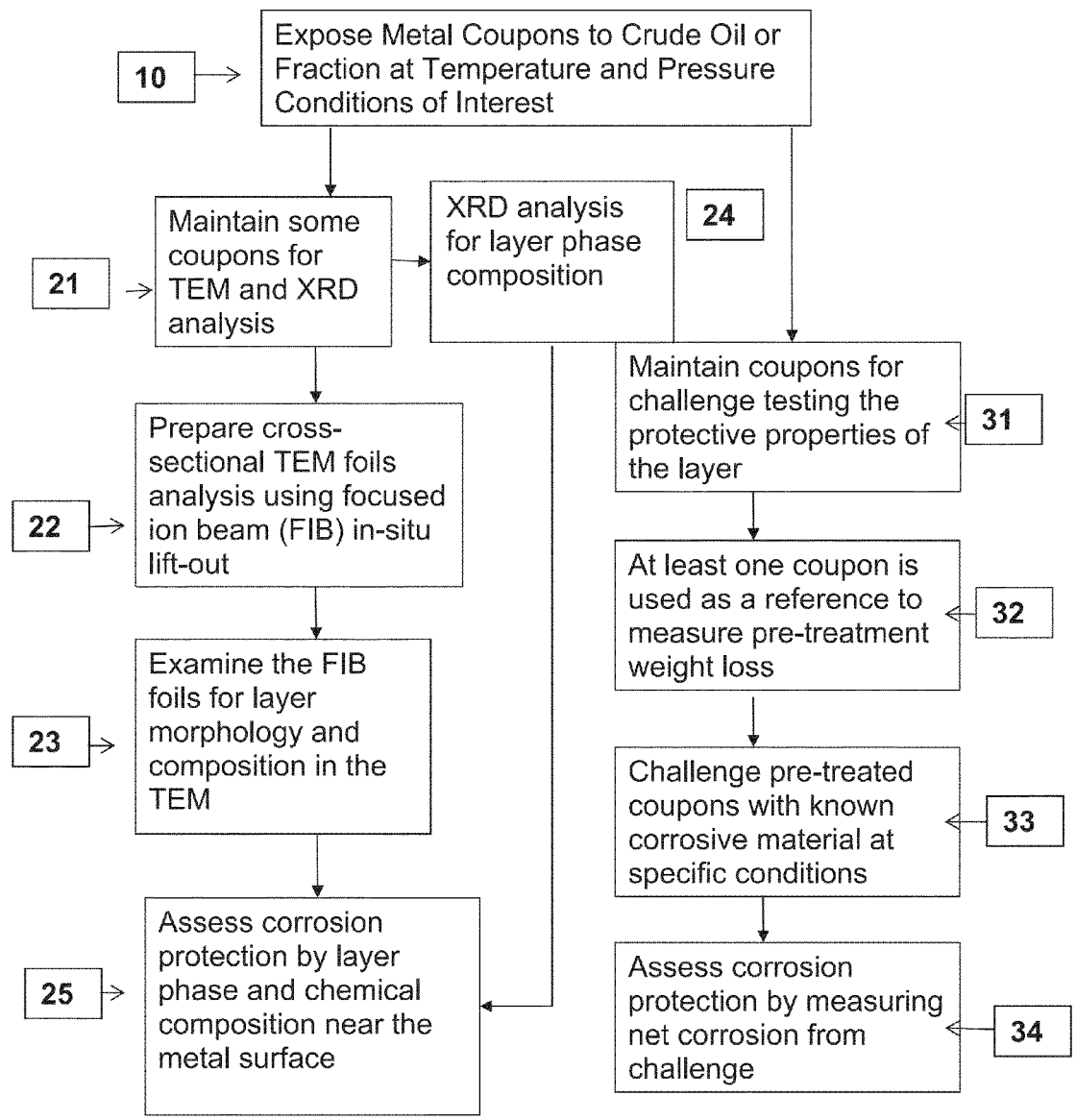
FIG. 1 summarizes the protocol for identifying and measuring the corrosion protection provided by the components in crude oil or their fractions in accordance with the presently disclosed subject matter.

The presently disclosed subject matter will now be described in greater detail with respect to the figures. Each crude oil or crude fraction to be evaluated undergoes explicit testing. With reference to FIG. 1, the two phase test approach starts with a pre-treatment phase step 10 to form the desired corrosion protective layer for evaluation. The pre-treatment phase step 10 requires pre-treating the steel samples in a fluid to be evaluated for forming the protective layer for a period of 24 hours. It is contemplated that the pre-treatment period may be less than or more 24 hours provided sufficient time is provided to form the protective layer. The fluid is a whole crude oil, a crude oil fraction, or other derived oil.

During the 24-hour pre-treatment phase corrosion protective layers containing iron sulfide are generated on steel sample surfaces by exposure to the evaluated crude oil or crude fractions. The crude oil or fraction is heated in a laboratory type stirred reactor (Parr 4520, 1 liter) to a temperature representative of the expected field operating conditions. Although the temperature range for refinery crude units is typically 200-440° C., these extremes are usually not required in practice. At the upper end of this temperature range, naphthenic acid decomposes and at the lower end naphthenic acid corrosion is not active. Therefore, for refinery crude units, a pre-treatment temperature range of 250-375° C. is typically sufficient. The actual process streams falling within this range will, depend on the specific product being made and the nature of the crude or fraction slate feed. If it is desired to obtain corrosion information over wide range of temperatures, it may be necessary to run more than one laboratory test temperature. In many cases, information may be available that defines the temperature range with the highest corrosivity. In addition to the test fluid, metal coupons are also installed in the reactor. The coupon metallurgy should be representative of the field metallurgy. It is acceptable to include multiple coupon metallurgies in a single reactor exposure.

It is contemplated that the steel samples may be either rectangular coupons or circular rings. The metallurgies of the coupons and optional rings are matched as closely as possible. At least two samples of each steel are pre-treated for use in connection with the presently disclosed subject matter and second phase analysis. In particular, at least one sample is used to perform analysis in accordance with the presently disclosed subject matter and one sample may be used for weight loss measurement in a manner disclosed by Bota.

The illustrative examples set forth herein utilize ring samples that are fabricated from carbon steel (ASTM A-106) and low carbon steel alloy (carbon alloying in the range of approximately 0.05-0.15%). The metallurgy of carbon steel rectangular coupons is in accordance with ASTM A516 grade 70 pressure vessel steel. Carbon steel ring and rectangular metallurgy are abbreviated as CS. An example of a low carbon steel alloy is described by ASTM specification SA-335 P5 material with approximately 5% chromium and 0.5% molybdenum (abbreviated as 5-Cr).

The presently disclosed subject matter analyzes the availability of well-adhered oxygen-containing layers as a mechanism to reduce naphthenic acid corrosion from crude oil or crude oil fractions. The oxygen-containing layer is within 1 micron of the steel-layer interface. In cases where the corrosion protective layer is multi-layered, the oxygen is present in the layer closest to the steel. A method to assess the oxygen content of the corrosion protective layer and relate it to corrosion protection is disclosed. The presently disclosed subject matter relates observable corrosion protective layer morphology and phase composition to the direct measure of corrosion protection.

Following the pre-treatment phase step 10 at the desired temperature, at least two coupon samples are analyzed in accordance with the layer analysis methodology of the presently disclosed subject matter. In accordance with step 21 of the layer analysis methodology, samples are maintained for analysis using transmission electron microscopy (TEM) and x-ray diffraction (XRD). In step 22 of the layer analysis methodology, cross-section TEM foils of the corrosion protective layer are prepared. A submicron elemental assessment of the formed corrosion protective layer, most preferably within the first micron of the steel surface is necessary. For this reason, TEM/EDS technology is preferable for this submicron analysis rather than SEM/EDS analysis. However, any analysis method that provides the submicron information is satisfactory and well within the scope of the presently disclosed subject matter. The cross-section TEM foil of the corrosion protective layer is prepared by an in-situ focused ion beam (FIB) lift-out technique, as disclosed for example by Giannuzzi (e.g., Giannuzzi, "Introduction to Focused Ion Beams: Instrumentation, Theory, Techniques, and Practice," Springer, New York, 2005; and Giannuzzi, "Materials Research Bulletin," V32, 2007). These disclosures are incorporated specifically herein by reference in their entirety. In step 23, the layer morphology and composition are analyzed. This analysis of the corrosion protective layer morphology is accomplished using the TEM. The corrosion protective layer composition of the oils is analyzed using energy dispersive x-ray spectroscopy using the TEM instrumentation. One of the two samples saved in step 21 is used to perform XRD analysis in step 24. The XRD analysis is made directly on the exposed coupons with no additional mounting procedures. In step 25, the layer morphology and elemental composition obtained using TEM in step 23 and the layer phase composition obtained from the XRD analysis in step 24 are assessed to determine whether or not the coupon developed a corrosion protective layer after exposure to the fluid.

Coupons that were subject to the pre-treatment phase 10, but not used as part of the TEM and XRD analysis in steps 21, 22, 23, 24 and 25 may be used to assess the corrosion protection afforded by the formation of the corrosion protective layer on the coupon. This may be accomplished by measuring the "challenge" corrosion rate, as described by Bota, described above. The challenge testing process will now be described in greater detail. In step 31, coupons that were subject to a pre-treatment phase 10 are segregated for challenge testing. At least one of the coupons is used as a reference to measure pre-treatment weight loss in step 32. No further processing is performed on this coupon. In step 33, the non-reference coupons are challenged using known corrosive materials at specific conditions. In step 34, the corrosion protection afforded by the layer formed from exposure to the fluid is assessed. This is accomplished by measuring the net corrosion of the challenge. Those coupons experiencing a net weight loss when compared to the reference coupon underwent corrosion. The greater the weight loss, the lesser the corrosion protection provided by the layer. This technique can be used to confirm which compositions identified in step 25 afford greater protection. The presently disclosed subject matter is not dependent upon any particular method for evaluating the corrosion resistance of the formed corrosion protective layer. Although the data from this method for assessing corrosion resistance is provided herein as a means to demonstrate the methodology for assessing layer corrosion resistance, the two-phased approach of pre-treatment and challenge method is neither the inventive step nor a unique referee method. Other methods for evaluating the corrosion persistence may be applicable (ASTM G185-06 Standard Practice for Evaluating and Qualifying Oil Field and Refinery Corrosion Inhibitors Using the Rotating Cylinder Electrode). The following examples illustrate the layer analysis methodology and employ an iron sulfide chrome corrosion protective layer and naphthenic acid corrosion in the temperature range of 315-343° C. These conditions represent typical conditions in refinery crude distillation units. It is contemplated that the layer analysis methodology in accordance with the presently disclosed subject matter may be used with other chemistries or temperature ranges.

The availability of a spinel-type oxide layer at the metal/corrosion protective layer interface enables the formation of a layer providing protection from subsequent naphthenic acid corrosion. As described in the prior art, typical sources of oxygen are from air or water. The temperatures for refinery crude units are too high for water to be present as a liquid. Likewise, oxygen (air) and water must be excluded from the crude oil processing to prevent uncontrolled combustion. Since there is a possibility that very small amounts of dissolved oxygen may be present in the feeds reaching crude units, tests have been executed to assess the impact of dissolved oxygen. The testing used the previously described stirred reactor. The typical pre-treatment test protocol described by Bota, as described above, is to purge the reactor vapor space with nitrogen prior to applying reactor heating. The process of stirring and nitrogen purging would be effective in removing any dissolved oxygen in the liquid feed. Any water could be removed by venting the reactor once the temperature was higher than the water boiling point. Special tests were conducted to deliberately purge the reactor vapor space with compressed air prior to the pre-treatment. Using a test fluid with TAN of 0.1 mgKOH/g and sulfur of 0.35% at 343° C., as shown in Table 1, there was only minor change in the corrosion rate of carbon steel and 5-Cr coupons for a 24-hour exposure compared to the pre-treatment with the more typical nitrogen purge.

TABLE 1

Pre-Treatment Corrosion Rates (mpy): 0.1 TAN; 0.35% Sulfur at 343° C.

|  | CS | 5-Cr |
|---|---|---|
| Nitrogen purge | 23 | 29 |
| Air purge | 21 | 24 |

(mpy = metal loss rate in mils per year)

Accordingly oxygen-containing components in the crude oil (other than dissolved oxygen) enable the formation of this protective layer. In the following examples, the probable source of the oxygen is from either the native naphthenic acid found within the crude fraction or the added acid in the model systems. These examples are provided to demonstrate the applicability of the presently disclosed subject matter.

Examples with Model Systems for Pretreatment

Crude oils and some of their crude oil fractions typically contain several naturally occurring minor elements in addition to naphthenic acid and sulfur. An example is presented using model systems as the pre-treatment fluid. Other examples with real feed fractions will also be presented. The model systems utilize laboratory grade reagents where contamination from extraneous elements is minimized. The primary components contributing to corrosion are naphthenic acid and sulfur. A model pre-treatment fluid is synthesized from Tufflo™ 6056 (white oil manufactured by Citgo) and Tokyo Chemical Incorporated (TCI) commercial naphthenic acid to which reagent grade dodecyl sulfide (DDS) is added to provide the sulfur component. Model fluids with compositions and properties to the Tufflo 6056 and TCI acids should work equally well.

TABLE 2

Summary of Laboratory Corrosion Rates for Challenge
TAN = 3.5 mgKOH/g at 343° C.

| Example. No. | Reactor pretreatment conditions for hour pretreatment time | | | Pretreatment | | Challenged | | TEM/EDS oxygen at metal/layer interface? Yes/No - metallurgy | XRD results |
|---|---|---|---|---|---|---|---|---|---|
| | Fluid | TAN mgKOH/g | Wt % S | Pretreat Temp. (C.) | Corrosion rate (mpy) CS / 5Cr | | Corrosion rate (mpy) CS / 5Cr | | |
| 1 | Model 1 | 1.75 | 0 | 315 | 20 / 2 | | 288 / 0 | Yes - 5Cr — CS | — |
| 2 | Model 2 | 1.75 | 0.25 | 315 | 12 / 8 | | 100 / 12 | Yes - 5Cr — CS | — |
| 3 | Model 3 | 0 | 0.25 | 315 | 12 / 8 | | 64 / 64 | No - 5Cr — CS | — |
| 4 | G | 4.9 | 0.15 | 315 | 5 / 5 | | 120 / 10 | Yes - 5Cr Yes - CS | 5-Cr: Fe, $Fe_3O_4$, FeS(T) CS: Fe, $Fe_3O_4$ |
| 5 | A | 1.75 | 0.5 | 343 | 10 / 8 | | 25 / 2 | Yes - 5Cr — CS | 5Cr: Fe, FeS(T), $Fe_3O_4$ |
| 6 | C | 1.1 | 4.2 | 315 | 40 / 40 | | 60 / 40 | Yes - CS — 5Cr | CS: Fe, FeS(T), $Fe_3O_4$ |
| 7 | B | 0.1 | 1.9 | 343 | 15 / 10 | | 90 / 10 | No - 5Cr — CS | — |

Note:
The crystal structure of magnetite, $Fe_3O_4$ and chromite, $FeCr_2O_4$ are identical. XRD technology cannot distinguish one from the other.
The table entries for 5-Cr steel showing $Fe_3O_4$ could also include $FeCr_2O_4$ or primarily $FeCr_2O_4$. Entries showing FeS(T) are troilite.

TABLE 3

Challenge Corrosion at 343° C. with No Pre-Treatment For
TAN = 3.5 mgKOH/g

| | Carbon Steel | 5-Cr |
|---|---|---|
| TAN = 3.5 mgKOH/g | 320 mpy | 80 mpy |

Figure 2A:
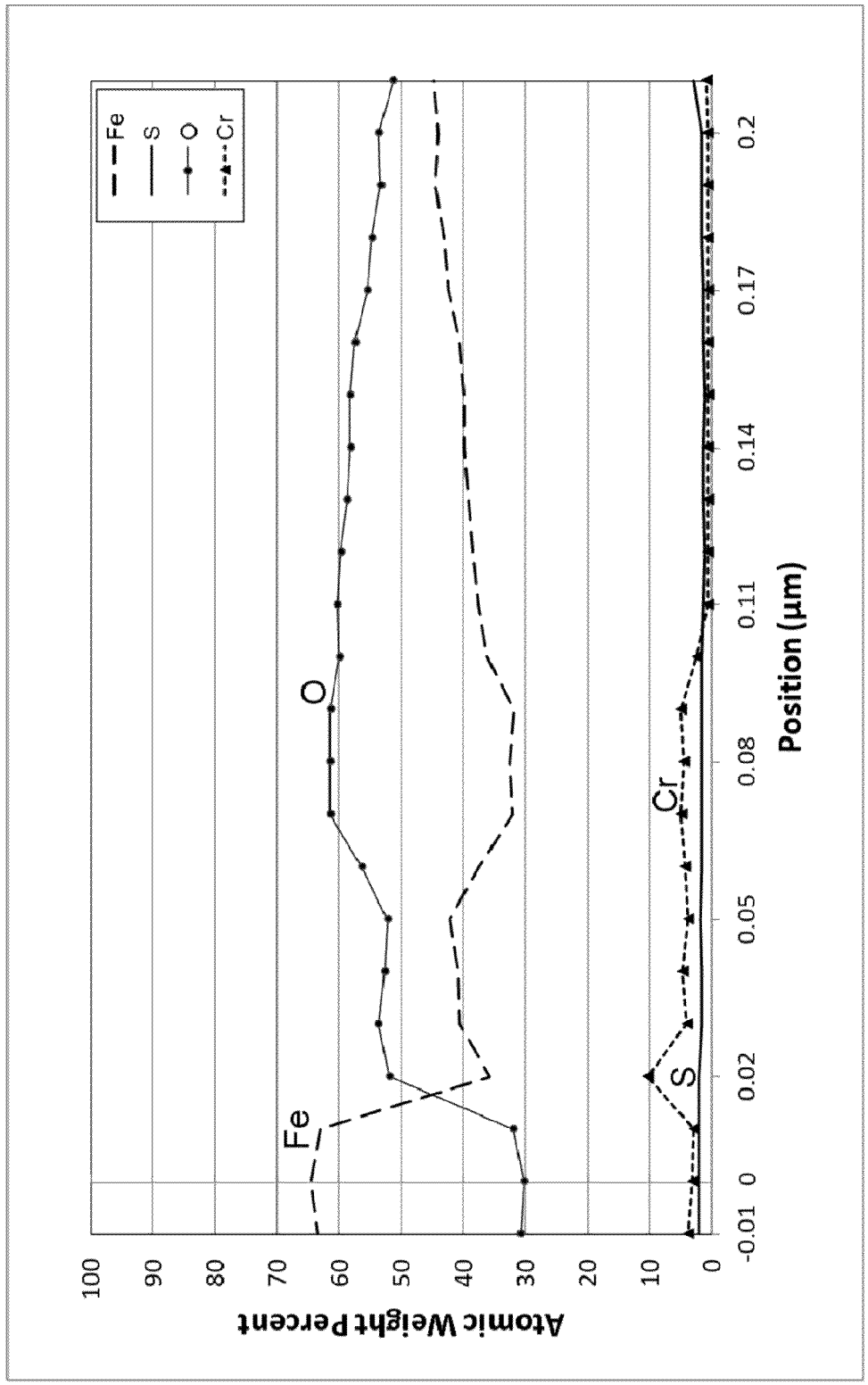
Figure 2B:
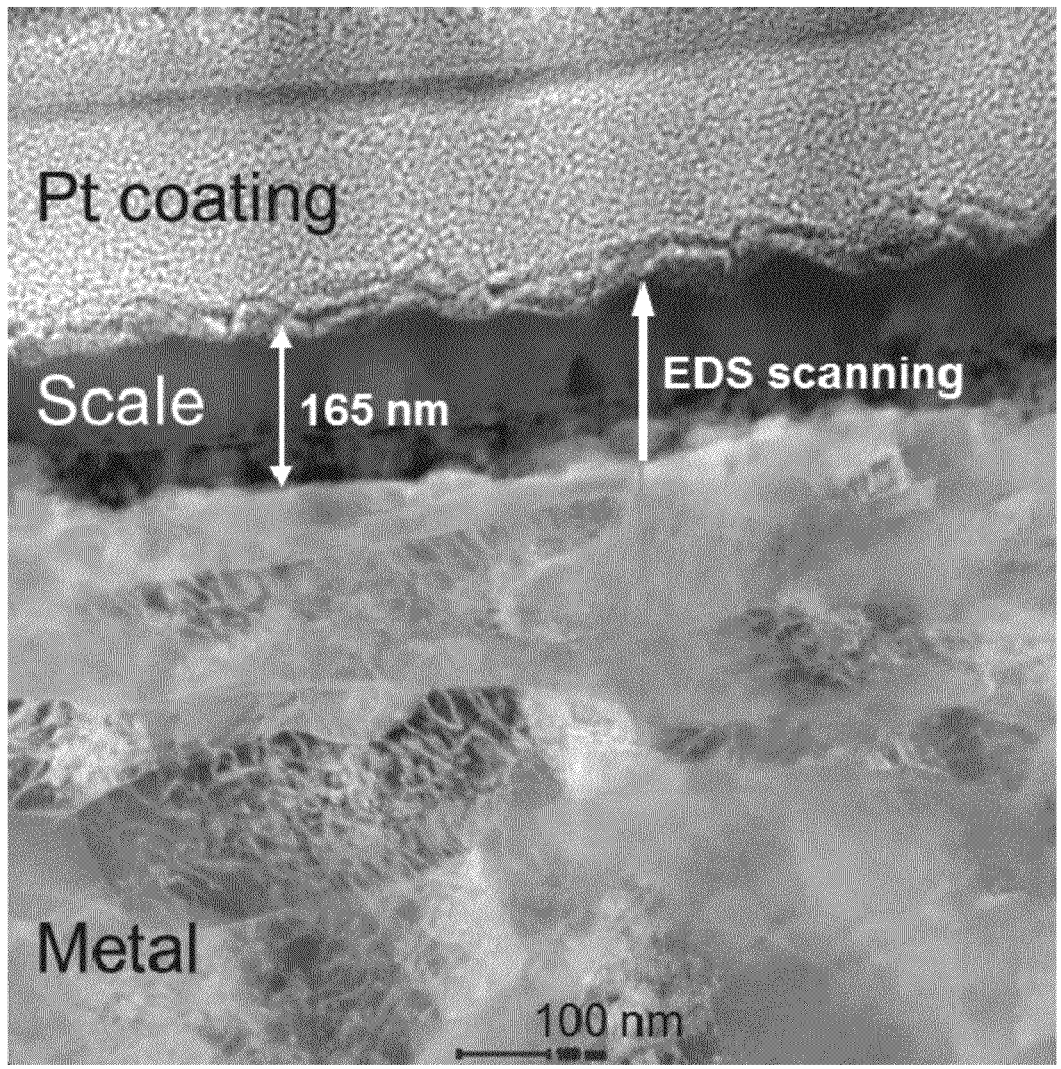
FIG. 2B illustrates its morphology using TEM. The layer was created on 5-Cr steel after pre-treatment at 315° C. with a model system having a TAN of 1.75 mgKOH/g (ASTM Method D664) and no sulfur. These figures relate to Example 1 of Table 2.
Figure 3A:
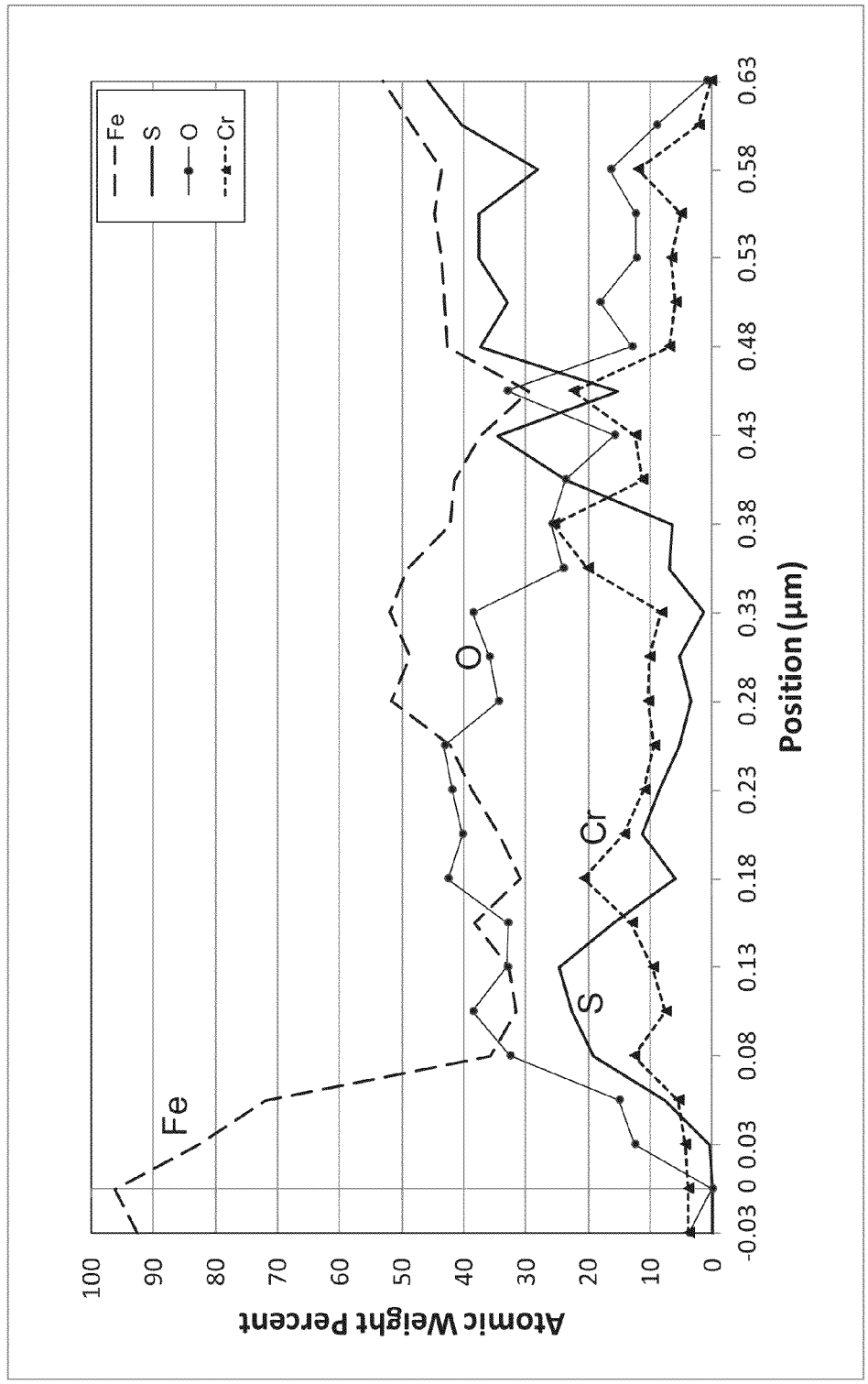
Figure 3B:
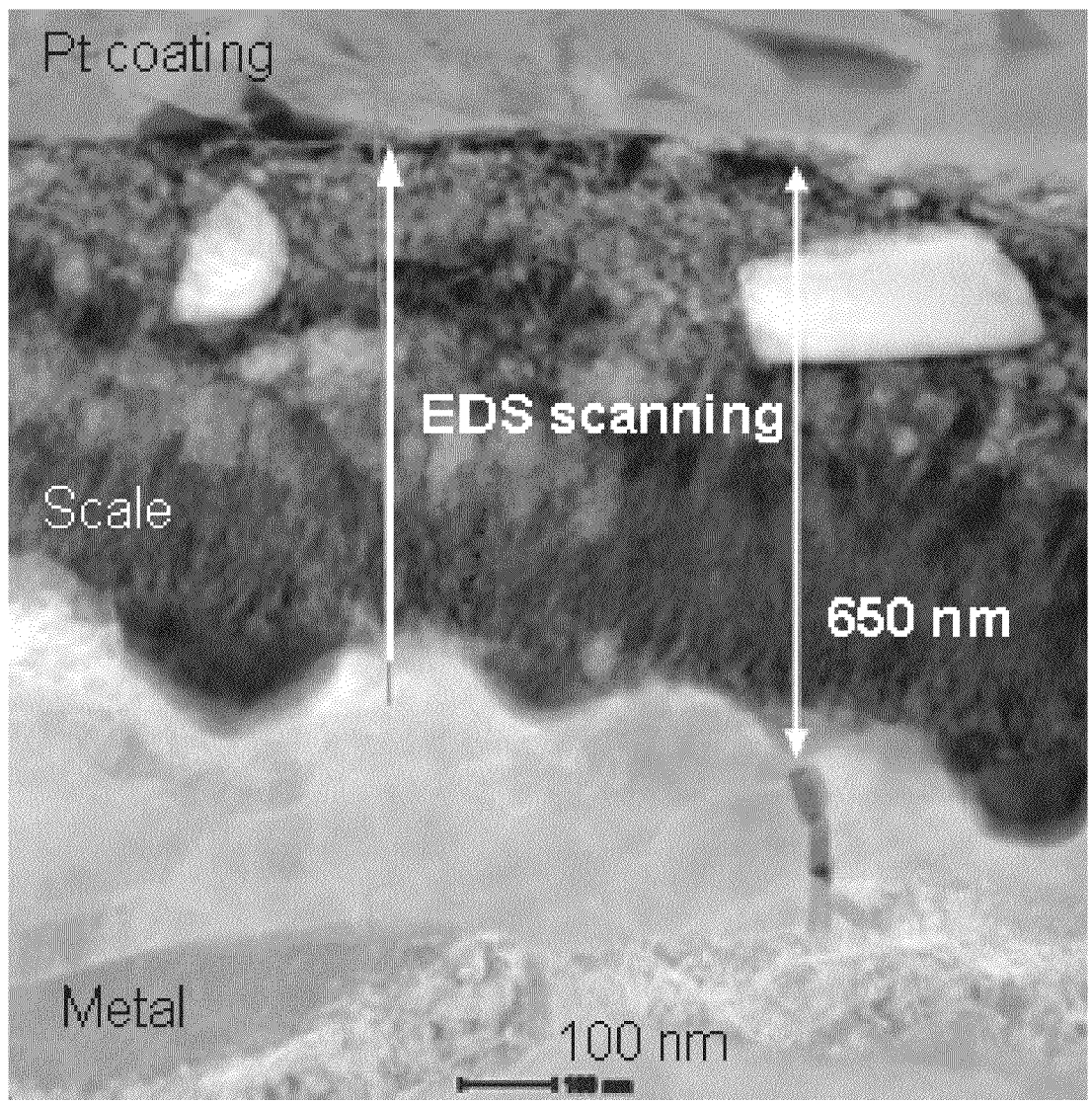
FIG. 3B illustrates its morphology using TEM. The layer was created on 5-Cr steel after pre-treatment at 315° C. with a model system having a TAN of 1.75 mgKOH/g and weight percent sulfur of 0.25. These figures relate to Example 2 of Table 2.
Figure 4A:
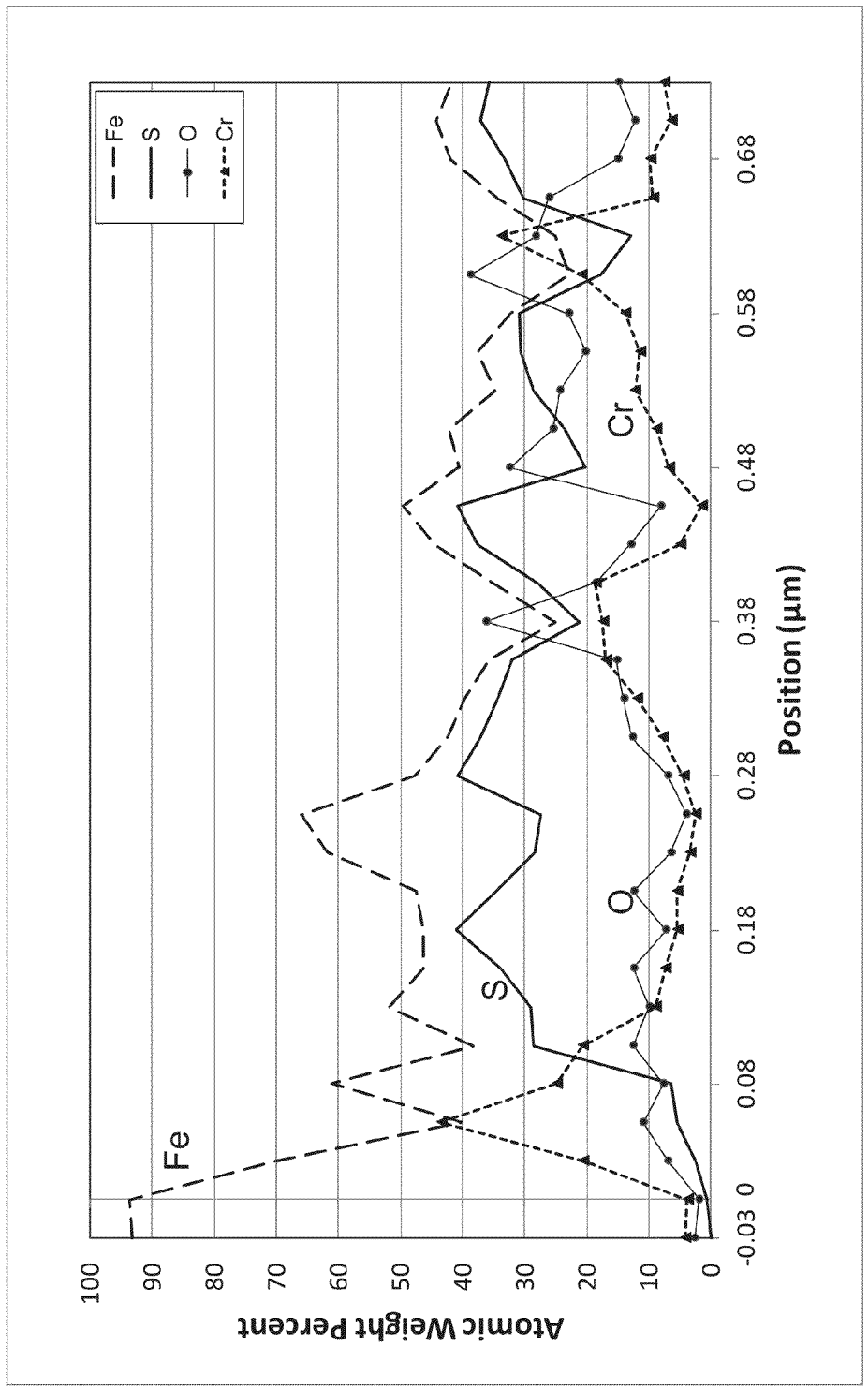
Figure 4B:
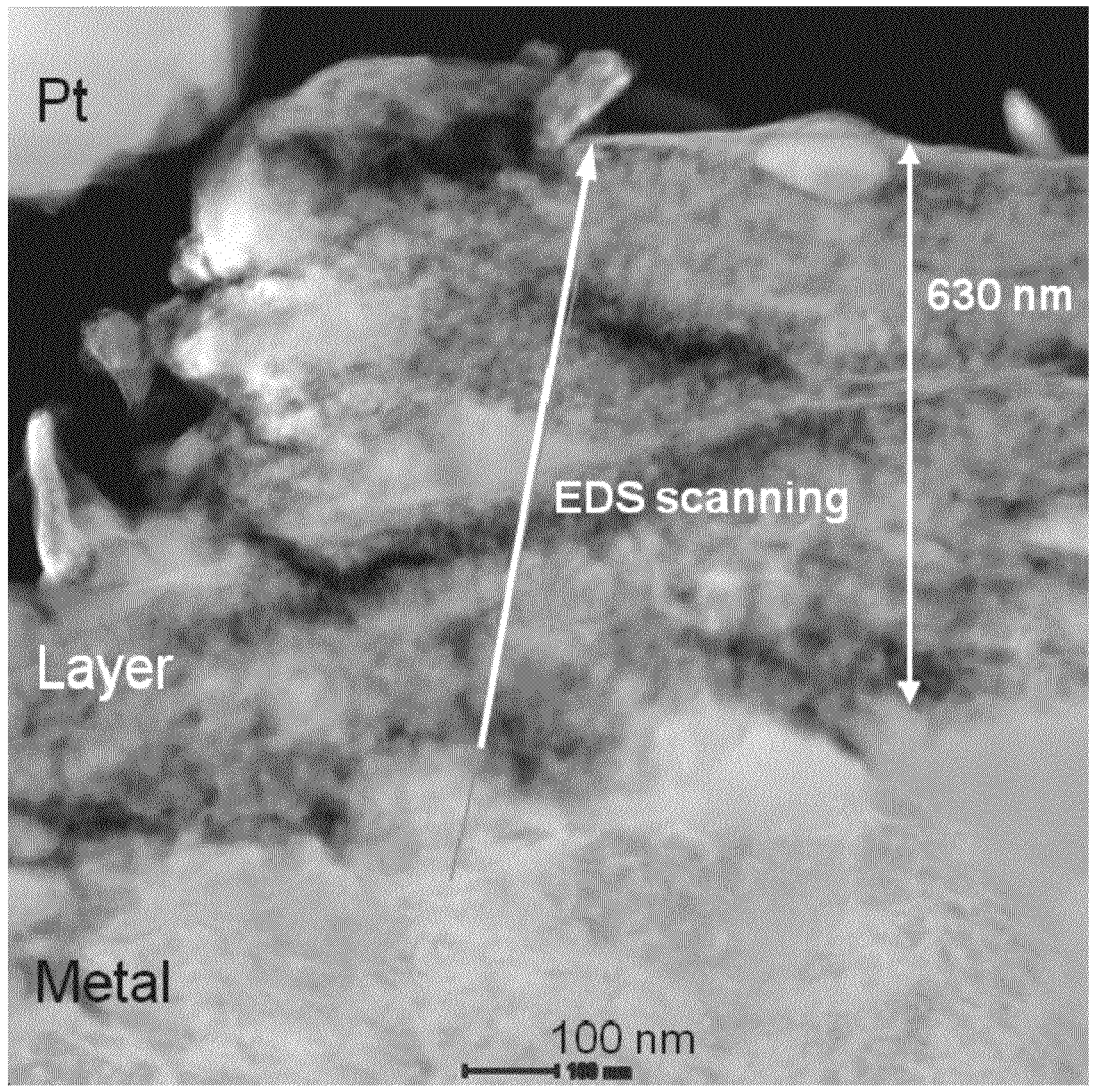
FIG. 4B illustrates its morphology using TEM. The layer was created on 5-Cr steel after pre-treatment at 315° C. with a model system having no TAN and weight percent sulfur of 0.25. These figures relate to Example 3 of Table 2.

Table 2 lists pre-treatment and challenge corrosion rates for all of the examples cited in the figures. The table include the three cases of pre-treatment with model systems: Example 1 with TAN=1.75 mgKOH/g and no sulfur; Example 2 with a TAN of 1.75 mgKOH/g and sulfur of 0.25% (weight percent); and Example 3 with no naphthenic acid (TAN=0) and sulfur of 0.25%. The pre-treatment temperature for these three examples is 315° C. FIGS. 2, 3, and 4 respectively show the near surface TEM image for the 5-Cr metallurgies of the corrosion protective layer (the "B" image in the figures) and elemental composition variation across the corrosion protective layer from EDS (the "A" plot in the figures) for Examples 1, 2, 3 in accordance with steps 21-25 of the corrosion protective layer analysis methodology. For these figure and others that are described as "after pre-treatment", the data shown are for coupons that have only been exposed to the FIG. 1 step 10 pre-treatment and have not been subjected to the naphthenic acid challenge.

The EDS line profile is conducted at the location indicated in the TEM image. The scan initiates within the metal and continues into the corrosion protective layer. The surface of the metal is located at the abscissa position of 0 and is noted on the figures with a vertical line. Negative locations are positioned within the metal and positive locations are positioned within the corrosion protective layer. The metal to corrosion protective layer transition is demarked by the rapid reduction of iron and an increase in the other elements. The elemental concentrations produced by EDS in the TEM should be interpreted qualitatively due to the limitation of EDS analysis (especially for light elements like oxygen). With its lighter molecular weight, the oxygen measurement will be more variable than the other elements of interest. The meaning of qualitative EDS concentration implies a relative concentration assessment rather than an absolute value of the concentrations. The precise concentration of the various elements is secondary compared to relative concentrations. The location of the elements in the corrosion protective layer with respect to the metal surface, and the type of phase formed are of more significance than the absolute elemental concentrations. In the examples that follow with model systems and those examples with real feed fractions, the following results will be observed:

a) When conditions are favorable for the formation of a spinel-type oxide at the metal surface, corrosion protection to subsequent naphthenic acid corrosion is achieved; and b) When conditions do not enable the formation of a spinel-type oxide at the metal surface, corrosion protection to subsequent naphthenic acid corrosion is governed by the deposition and nature of an iron sulfide corrosion protective layer.

c) When conditions enable the formation of both the spinel-type oxide and iron sulfide layers, typically the oxygen will be immediately adjacent to the metal surface. Both layers may contribute to corrosion protection.

For Example 1, it is observed in FIG. 2 that the oxygen component dominates the elemental composition and is formed immediately adjacent to the steel surface for the case when only naphthenic acid was added to the pre-treatment phase (no sulfur during pre-treatment). With corrosion rates summarized in Table 2, Example 1 had a naphthenic acid challenge corrosion rate of 0 mpy. The challenge corrosion rates for Examples 2 and 3 increased with a corresponding decrease in relative oxygen concentration present at the steel surface as shown, respectively, in FIGS. 3 and 4. In FIG. 3, oxygen is available from the naphthenic acid and the resulting oxygen concentration near the metal surface is dominant compared to the concentrations of sulfur and chromium. With the addition of sulfur, both the oxygen and sulfur will compete to form a corrosion protective layer with the metal surface. Therefore, the oxygen concentration at the surface is lower in Example 3, as shown in FIG. 3 compared to Example 2 shown in FIG. 2 with no sulfur. In FIG. 2, the oxygen concentration dominates the iron; whereas in FIG. 3, the oxygen concentration is either comparable or lower than the iron concentration. In FIG. 4, the case with no naphthenic acid in the pre-treatment, the sulfur concentration is significantly higher than oxygen right at the metal/corrosion protective layer interface. The profile of oxygen in FIG. 4 indicates that the most significant oxygen concentration is not at the metal surface which is consistent because there is no naphthenic acid in the sample.

Figure 5A:
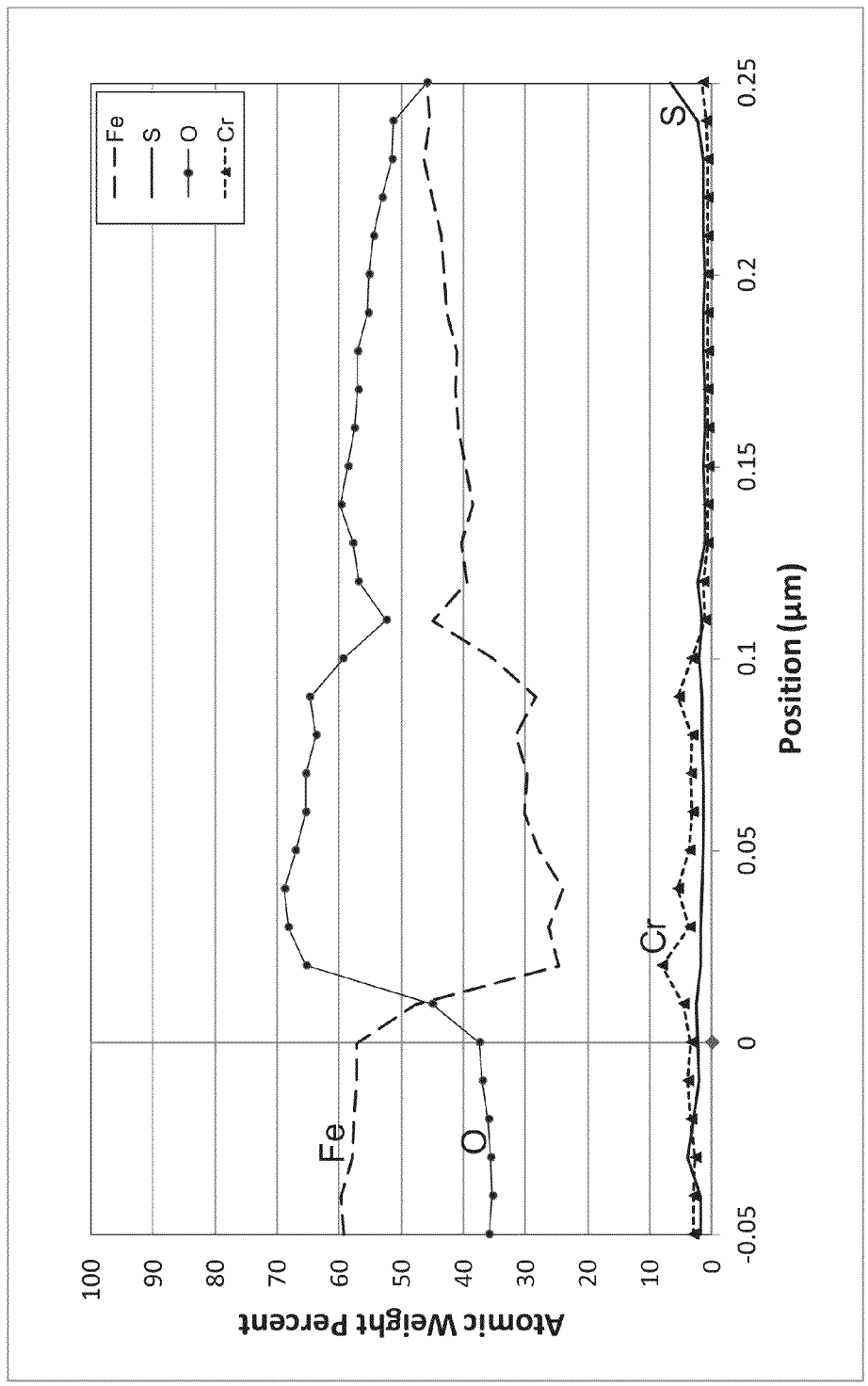
Figure 5B:
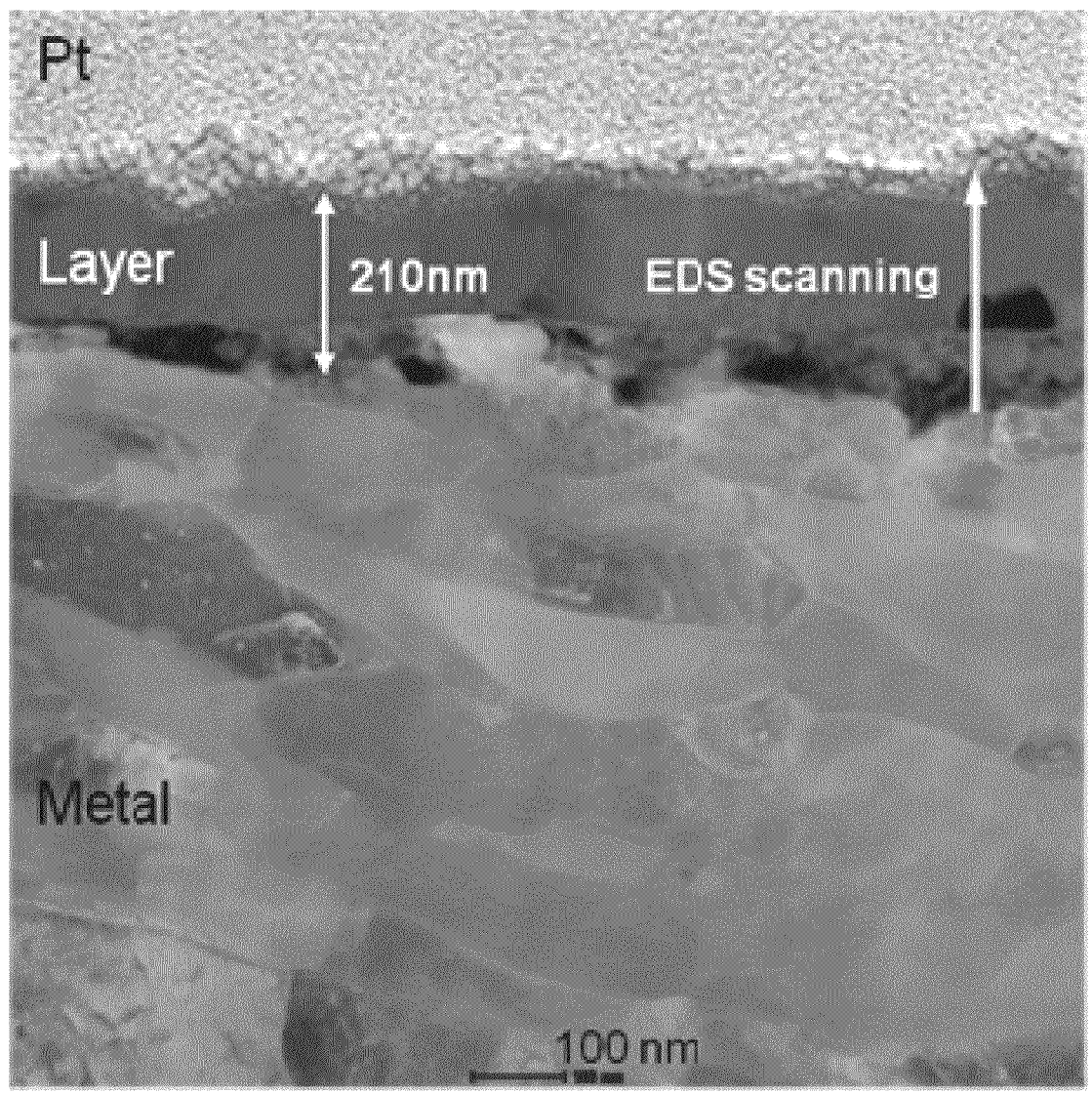
FIG. 5B illustrates its morphology using TEM. This layer was originally created on 5-Cr steel during pre-treatment. Pre-treatment of the ring coupon was with a model system having a TAN of 1.75 mgKOH/g and no sulfur. These figures relate to Example 1 of Table 2.

FIG. 5 presents the TEM/EDS data for the 5-Cr ring coupon corresponding to Example 1 after it was challenged consistent with FIG. 1 step 33. The corresponding pre-treatment TEM/EDS data are shown in FIG. 2. Comparing the two results, it is observed that there is very little change that occurs to the elemental composition of the corrosion protective layer at the metal surface as a consequence of the naphthenic acid challenge. This observation demonstrates that the protective corrosion protective layer formed during the pre-treatment phase survives the 24-hour naphthenic acid challenge.

These results with model systems demonstrate that protection to naphthenic acid corrosion improves with increased oxygen concentration in the corrosion protective layer at the metal/layer interface. It is also observed in Example 1 that for carbon steel a modest protective corrosion protective layer formed (challenge corrosion rate of 288 mpy compared to the 320 mpy corrosion with no pre-treatment (see Table 3)). Although the pre-treatment of carbon steel for Examples 2 and 3 also provides corrosion protection, the benefit is greater for the 5-Cr steel, as shown in Table 2 by a comparison of the challenged corrosion rates. In FIG. 2, it is also observed that chromium is present in the layer close to the metal surface. Therefore, the presence of elements, such as chromium, is also necessary to optimize the protection of the formed layer. Although it is preferable that the formation of a protective layer consisting of a magnetite-type and/or a chromite-type spinel where an oxygen component must form immediately adjacent to the steel, the absence of chromium still enables a lesser degree of corrosion protection. Examples that follow with real feed fractions provide additional demonstration.

Examples with Crude Oil Fractions for Pretreatment

Figure 6A:
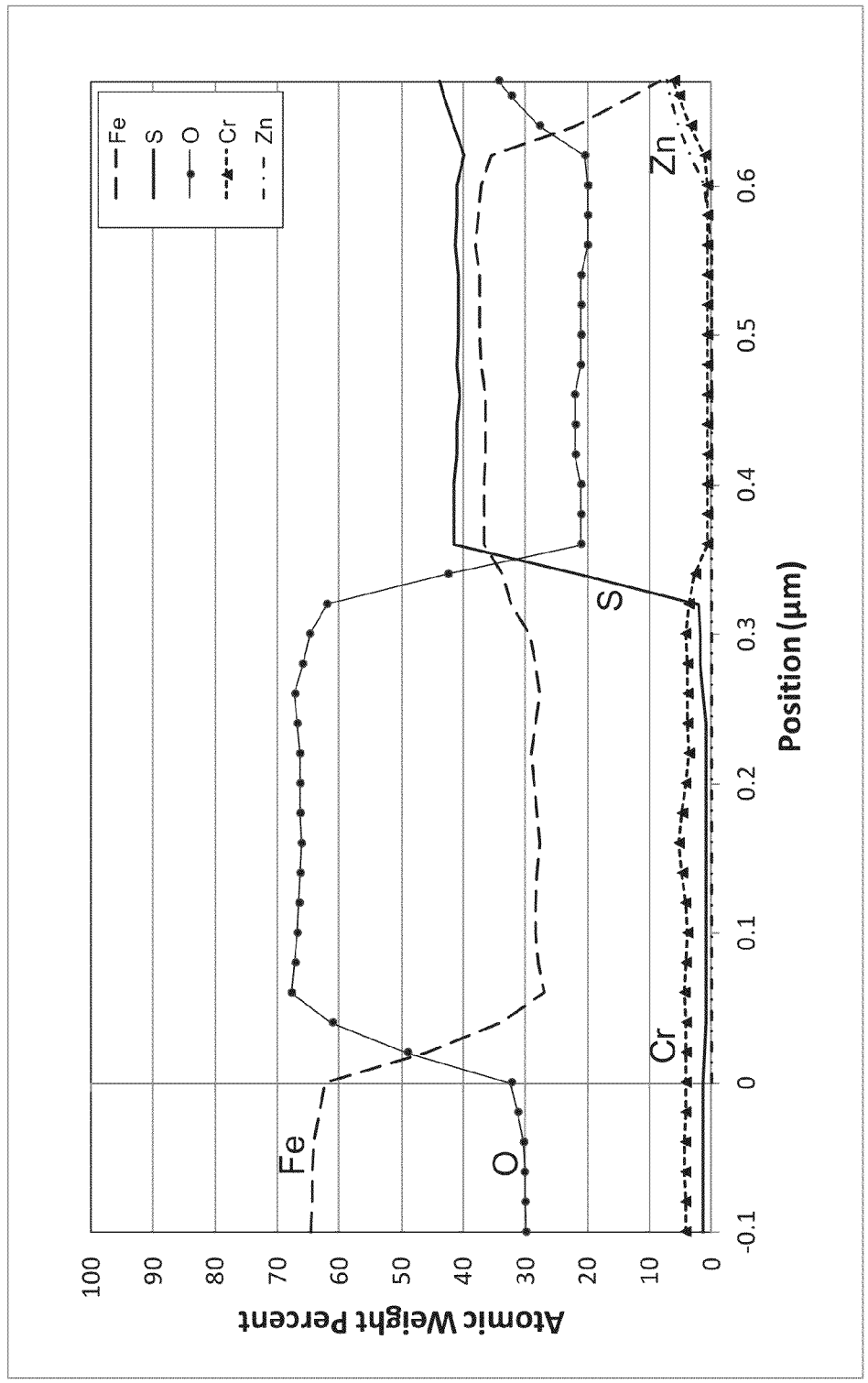
Figure 6B:
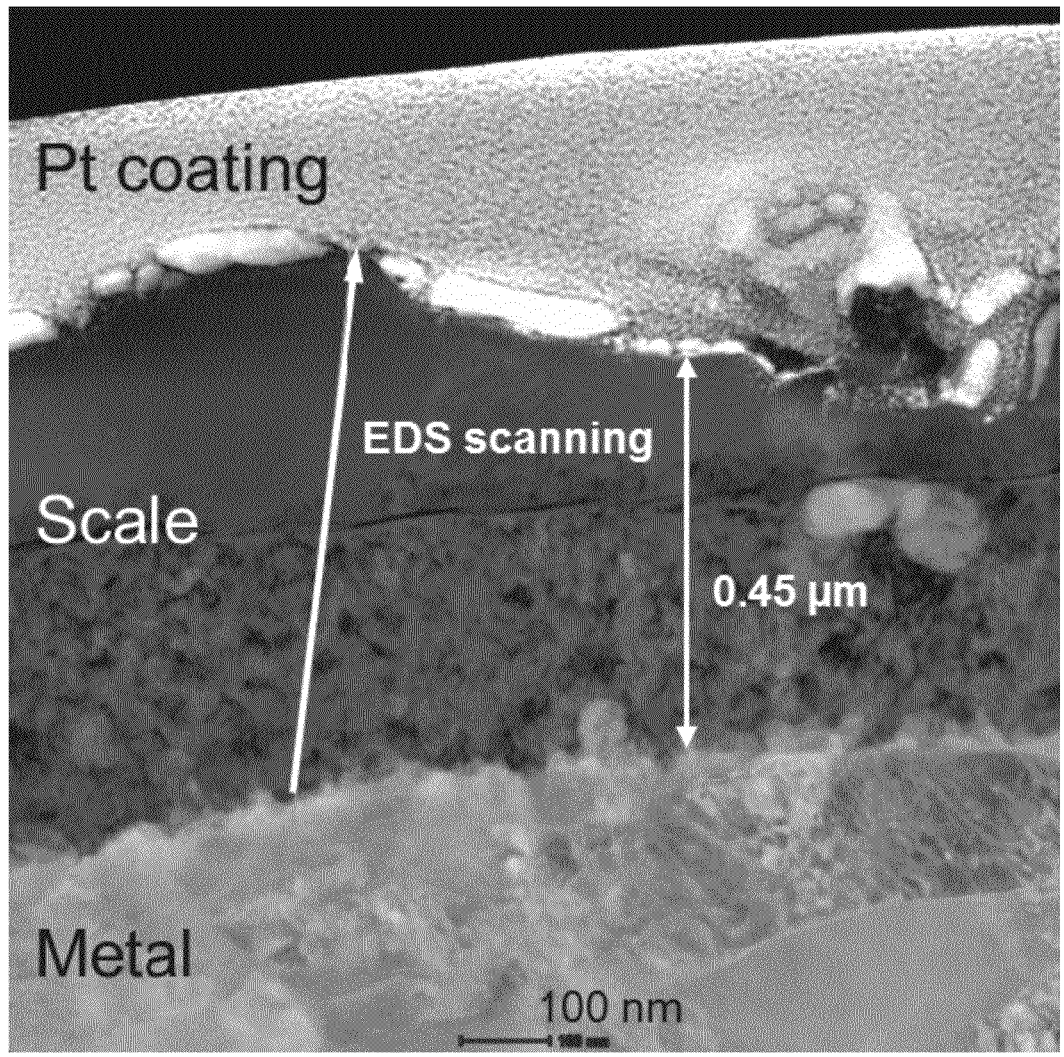
FIG. 6B illustrates its morphology using TEM. The layer was created on 5-Cr steel after pre-treatment at 315° C. with crude fraction G having a TAN of 4.9 mgKOH/g and weight percent sulfur of 0.15. These figures relate to Example 4 of Table 2.

Example 4 illustrates the pre-treatment with a vacuum gas oil fraction G. The results with the real feed fraction G on 5-Cr metallurgy are shown in FIG. 6. This vacuum gas oil fraction has a TAN of 4.9 mgKOH/g and sulfur weight percent of 0.15%. Based on prior art NACI type of analysis (Craig et. al), the expectation is that this crude fraction would experience naphthenic acid dominated corrosion. Because of the low sulfur concentration compared to the very high acid content, any layer that would form would have limited mass and would not be protective. Unexpectedly, the fraction G forms a protective layer on 5-Cr steel with a low challenge corrosion rate of 10 mpy when the pre-treatment is done at 315° C., as shown in Table 2. This result is consistent with model systems that formed an oxygen-containing layer near the metal surface. Fraction G showed a high oxygen concentration compared to iron, chromium, zinc, and sulfur immediately adjacent to the metal surface. Similar to Example 1 with protective layer shown in FIG. 2, the presence of chromium is also observed in the layer close to the metal surface.

Figure 7A:
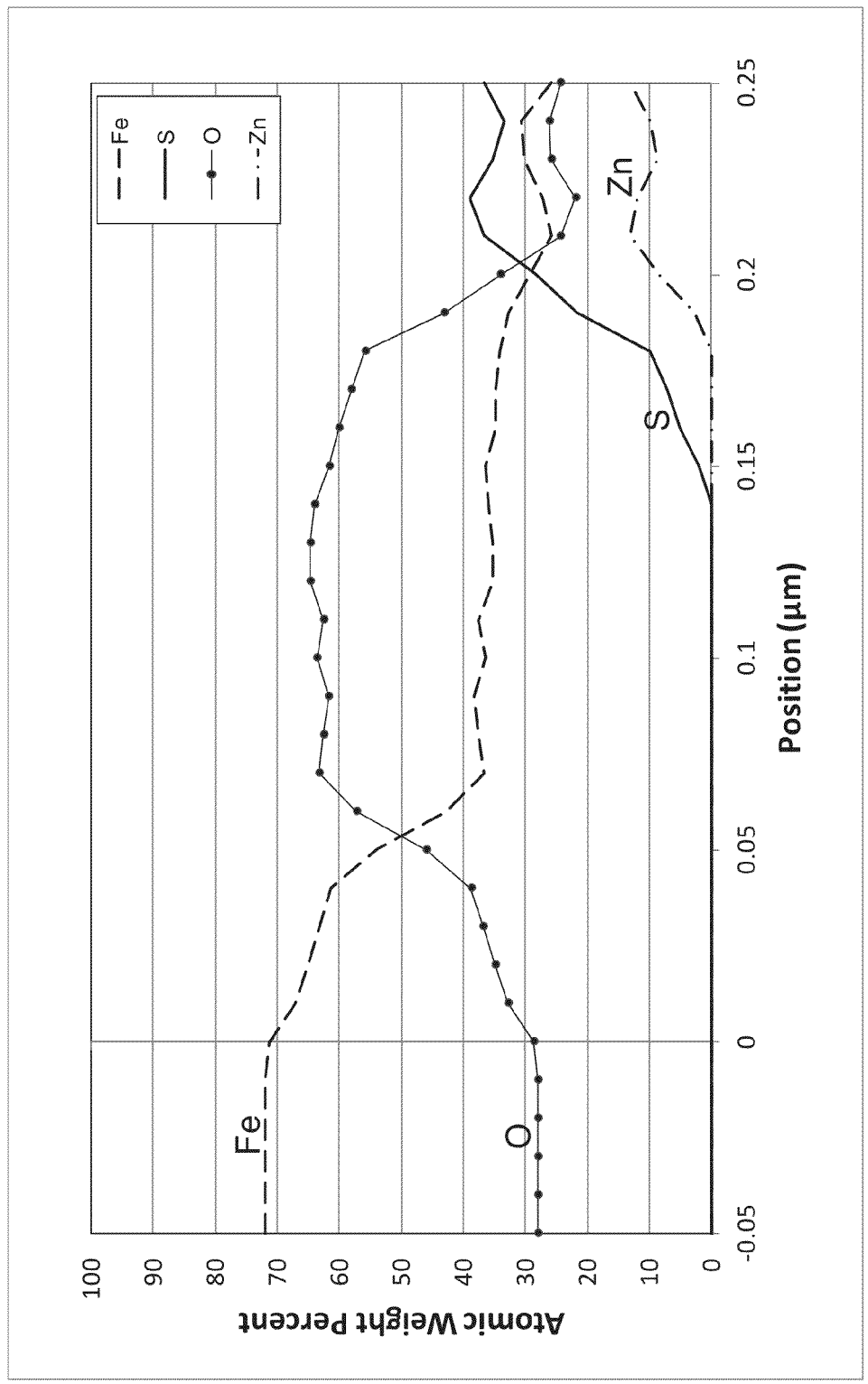
Figure 7B:
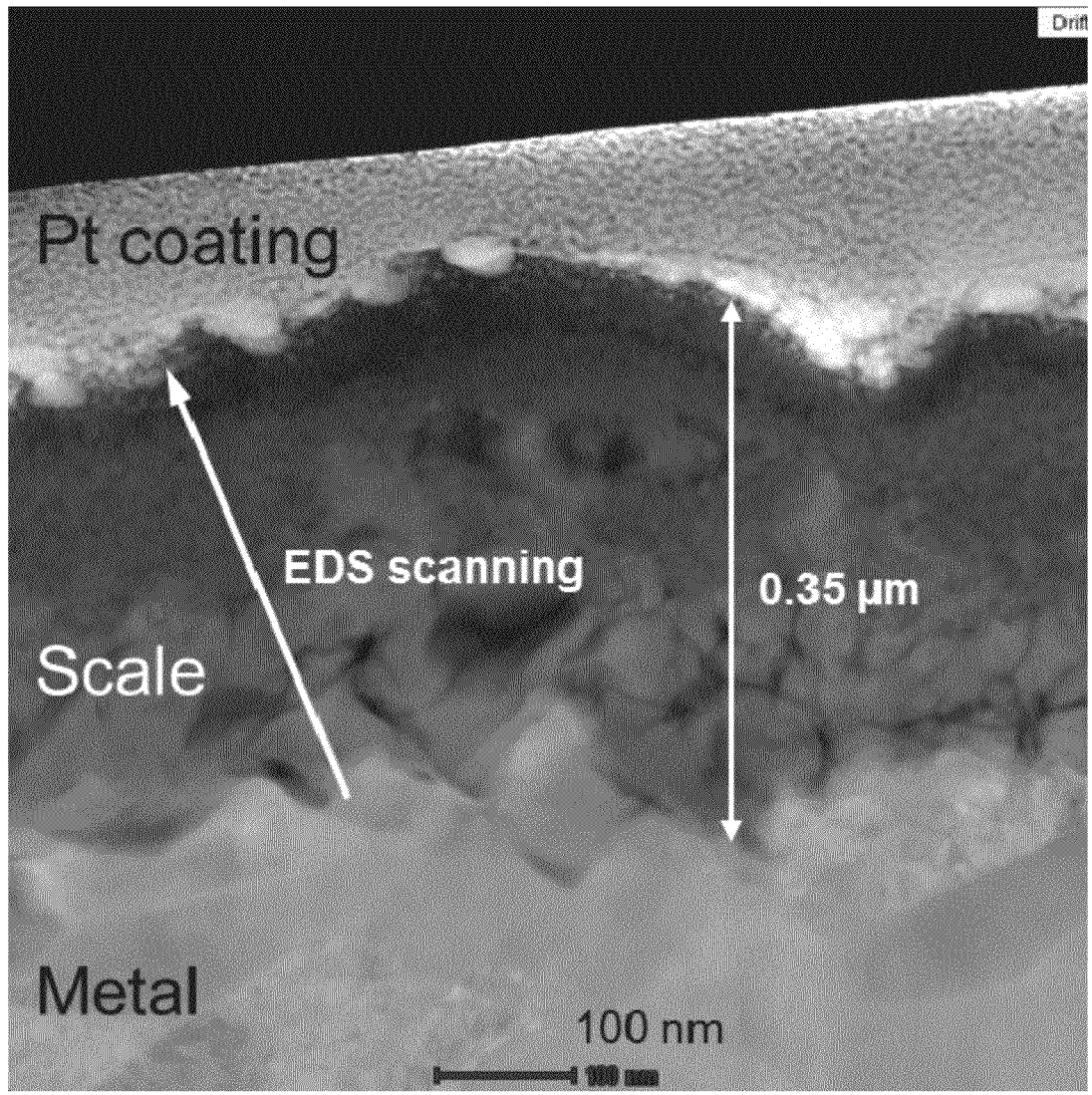
FIG. 7B illustrates its morphology using TEM. The layer was created on carbon steel after a pre-treatment at 315° C. with crude fraction G having a TAN of 4.9 mgKOH/g and weight percent sulfur of 0.15. These figures relate to Example 4 of Table 2.

The pre-treatment TEM and EDS results with fraction G on carbon steel are shown in FIG. 7. The challenge corrosion rate of 120 mpy indicates a measurable level of corrosion protection from the pre-treatment. Without pre-treatment, the corrosion rate would be 320 mpy (as shown in Table 3). Although the spinel-oxide layer formed during pre-treatment provides corrosion protection to carbon steel, the benefit is improved with chromium present in the metallurgy. In contrast to the 5-Cr result with crude Fraction G, the XRD carbon steel result could not detect appreciable iron sulfide in the layer. For crude Fraction G, the naphthenic acid concentration is sufficiently high compared to the sulfur enabling the formation of a protective oxide layer on 5-Cr.

Figure 8A:
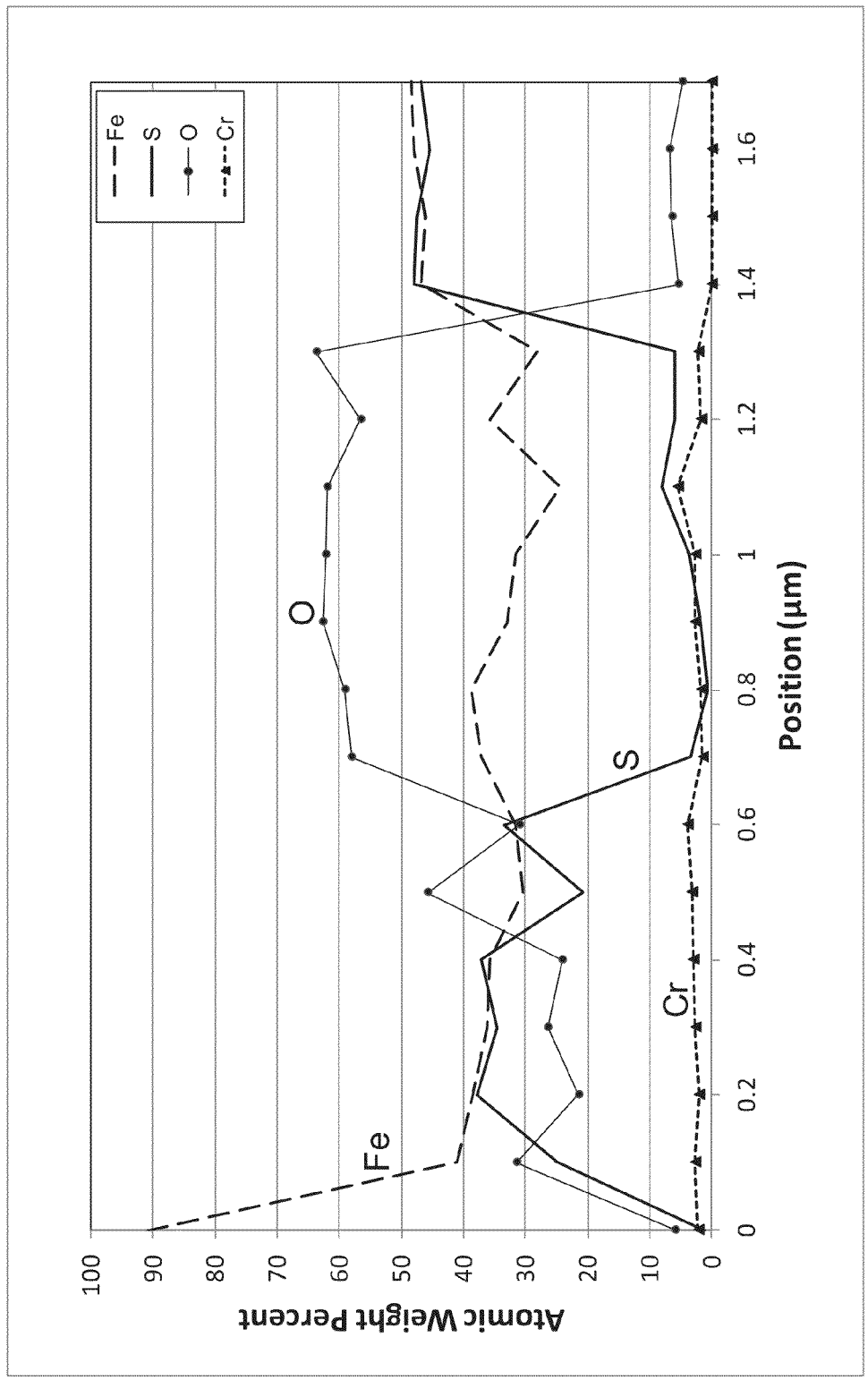
Figure 8B:
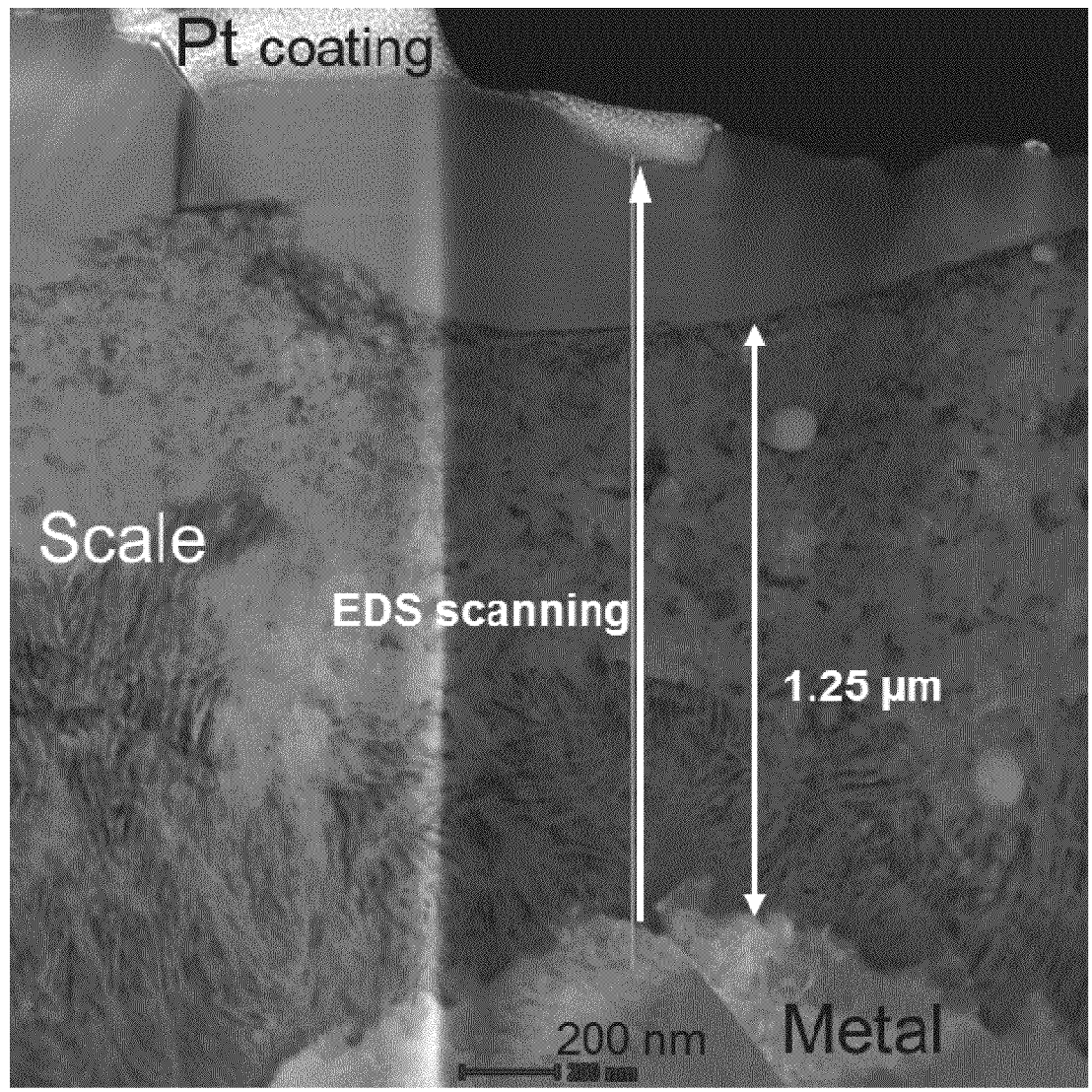
FIG. 8B illustrates its morphology using TEM. The layer was created on 5-Cr steel with a pre-treatment at 343° C. with crude fraction A having a TAN of 1.75 mgKOH/g and weight percent sulfur of 0.5. These figures relate to Example 5 of Table 2.

Example 5 presents results when pre-treatment is done with crude fraction A at 343° C. This example has naphthenic acid concentration similar to that of Example 2 with a slightly higher sulfur concentration of 0.5%. The pre-treatment temperature for Example 5 is 343° C. The respective challenge corrosion rates of 25 mpy and 2 mpy for carbon steel and 5-Cr steel demonstrate that crude fraction A does form a protective layer on these steels. For both steels, the challenge corrosion rate for the pre-treated steels is lower than the corrosion rates without pre-treatment. FIG. 8 presents the TEM and EDS analysis for the pre-treated 5-Cr coupon for Example 5. Adjacent to the metal surface, the overall oxygen concentration exceeds the sulfur level. The oxygen concentration competes favorably or exceeds the sulfur for most of the formed layer up to approximately 1300 nm from the steel surface. For this crude fraction, temperature, and metallurgy, the pre-treatment corrosion protection is enhanced by the availability of oxygen and the formation of a spinel-oxide layer near the metal surface.

The differences in pre-treatment temperatures, sulfur and naphthenic acid concentrations for Examples 2 and 5 demonstrate that other parameters may contribute to naphthenic acid corrosion protection. The procedures described herein provide a methodology for assessing naphthenic acid corrosion protection without the requirement to explicitly de-convolve the how those parameters interact.

Figure 9B:
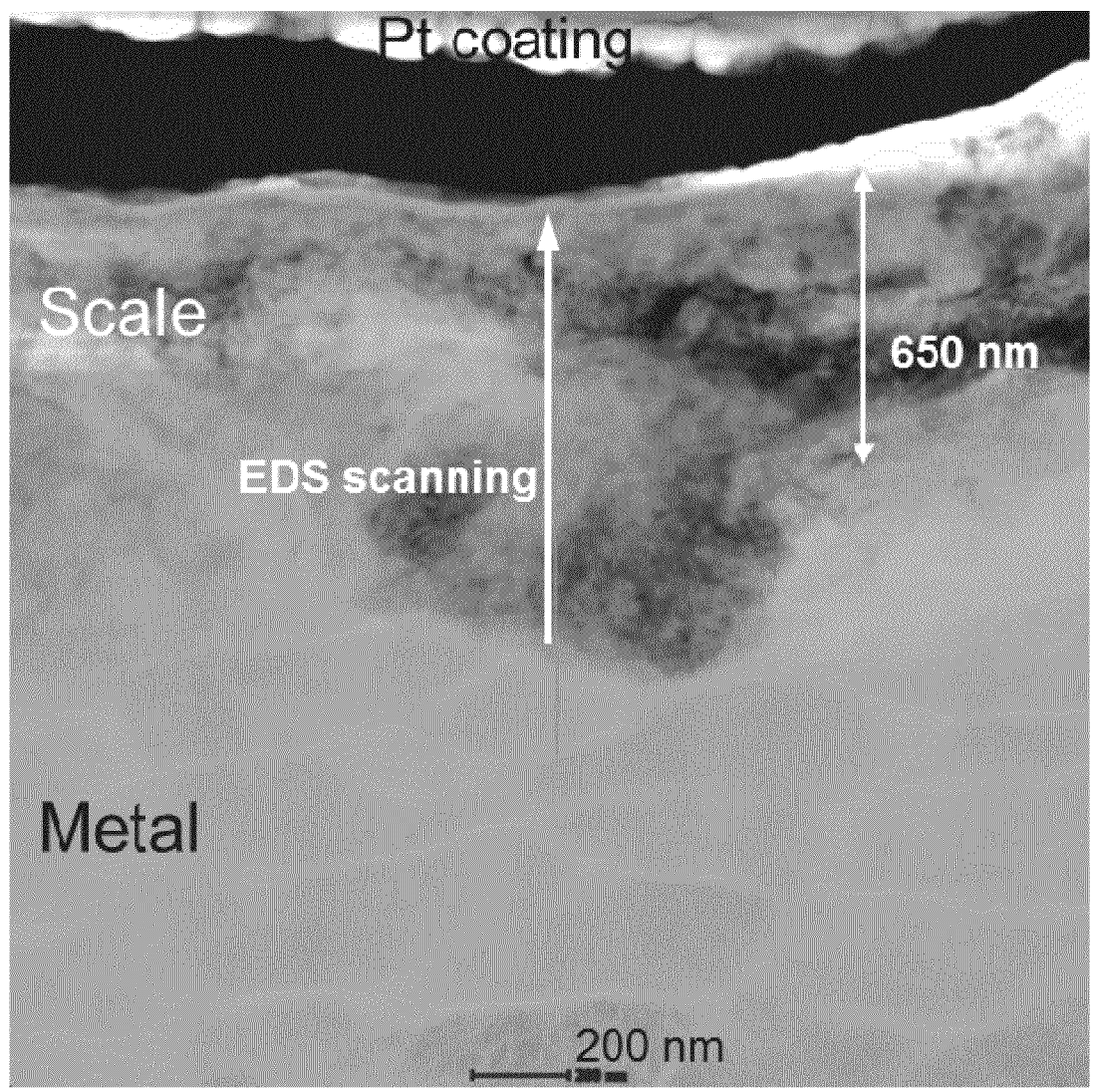
FIG. 9B illustrates its morphology using TEM. The layer was created on carbon steel with a pre-treatment at 315° C. with crude fraction C having a TAN of 1.1 mgKOH/g and weight percent sulfur of 4.2. These figures relate to Example 6 of Table 2.

Example 6 presents results with crude fraction C. In this example, the sulfur concentration of 4.2 percent is considerably higher than in the previous examples but the naphthenic acid TAN level of 1.1 mgKOH/gm is more closely aligned to the TAN of the model systems and crude fraction A. The carbon steel pre-treated challenge corrosion rate of 60 mpy is considerably reduced from the 320 mpy untreated corrosion rate (shown in Table 3). The 5-Cr corrosion pre-treated corrosion rate of 40 mpy is about half of the untreated corrosion rate. FIG. 9 presents the TEM and EDS analysis for the pre-treated carbon steel coupon for Example 6. Immediately adjacent to the metal surface, sulfur dominates the composition of the layer but oxygen is present. The XRD bulk analysis confirms the presence of magnetite. For this combination of temperature, metallurgy, and crude fraction, the TEM/EDS results confirms that the oxide layer should provide a good protection from naphthenic acid corrosion notwithstanding any contribution from the iron sulfide layer.

Figure 10A:
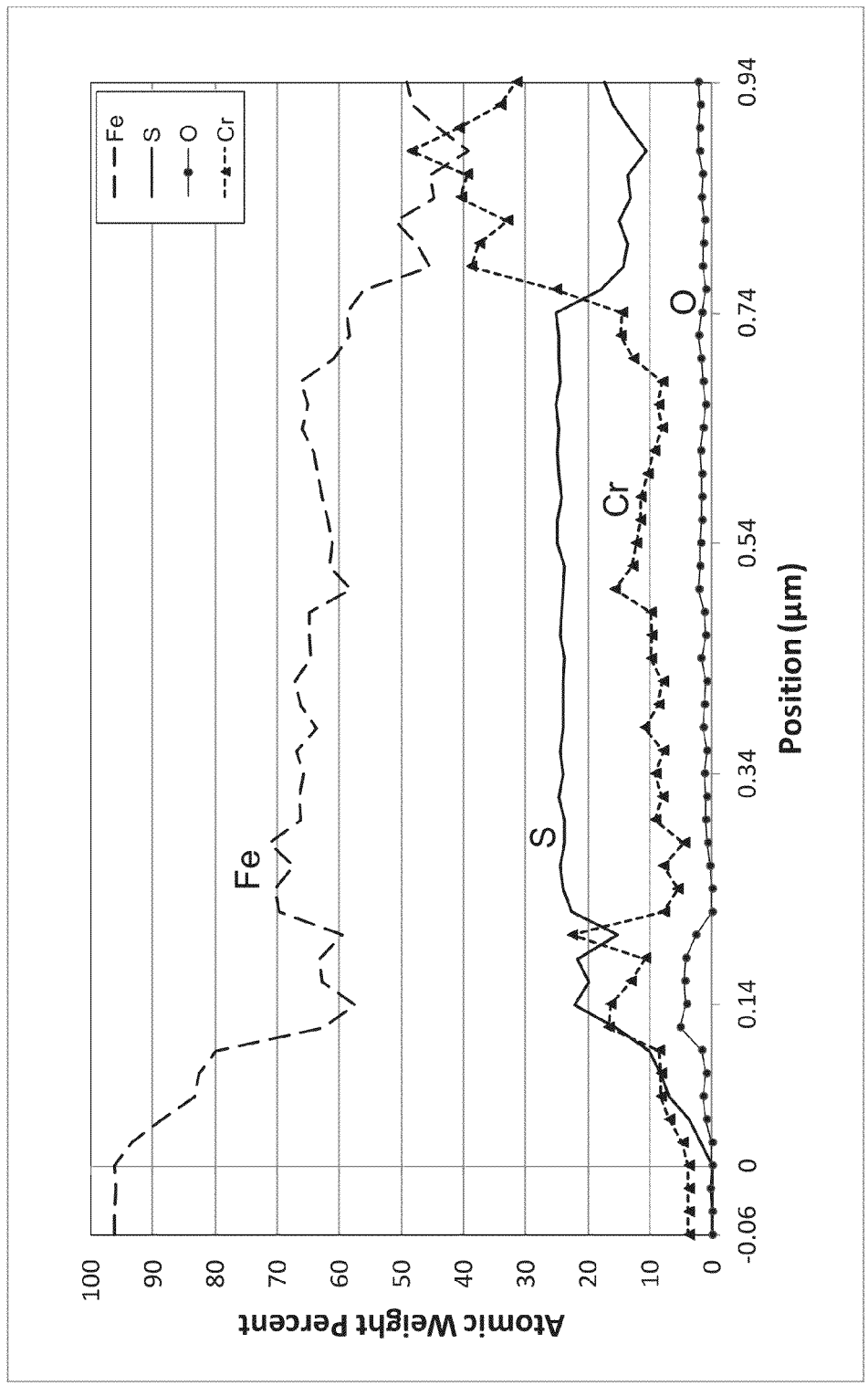
Figure 10B:
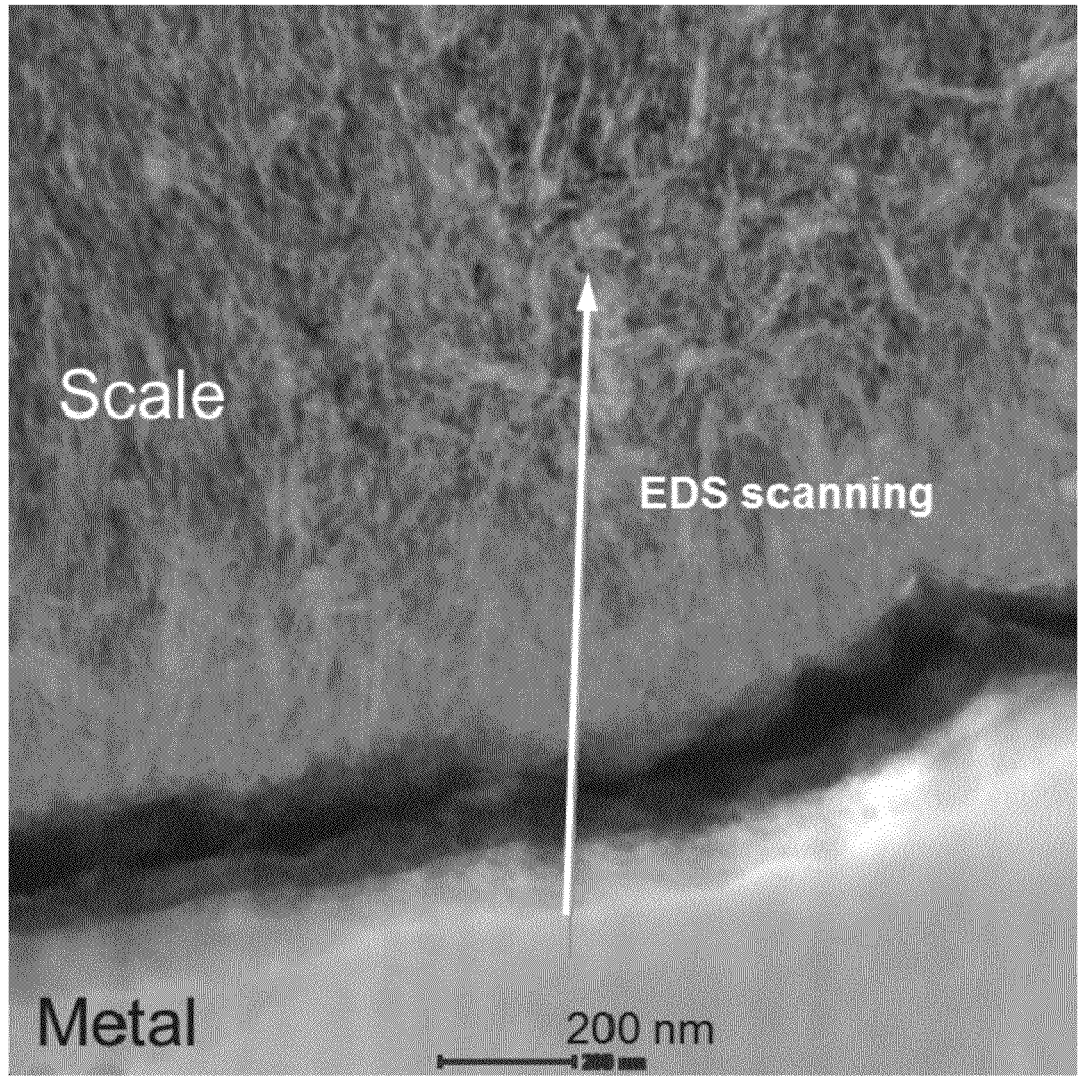
FIG. 10B illustrates its morphology using TEM. The layer was created on 5-Cr steel at 343° C. with crude fraction B having a TAN of 0.1 mgKOH/g and weight percent sulfur of 1.9. These figures relate to Example 7 of Table 2.

Example 7 presents results with crude fraction B. In this example, the sulfur concentration of 1.9 percent is considerably higher than the crude fraction A sulfur concentration; and the crude fraction B naphthenic acid concentration of 0.1 mgKOH/g is lower than for crude fraction A. As shown in Table 2, the carbon steel and 5-Cr challenge corrosion rates are 90 mpy and 10 mpy, respectively, for Example 7. FIG. 10 presents the TEM and EDS analysis for the pre-treated 5-Cr coupon for Example 7. Although the EDS results shows some oxygen near the steel surface, its thickness is less than 0.1 μm and its concentration is several fold lower than the sulfur and chromium levels in the layer near the metal surface. This result demonstrates that at elevated sulfur levels and very low naphthenic acid content, corrosion protection is also possible but due primarily to an iron sulfide (FeS—troilite) layer with at best, minimal contribution by an oxide layer. Crude Fraction A provides an example where corrosion protection is provided by the oxygen-containing layer at the metal surface. In contrast, with minimal oxygen, crude Fraction B derives its corrosion protection primarily from iron sulfide at the metal surface.

The examples presented herein using both the model systems and real feed fractions provide guidance on the limitations for the formation of the protective spinel-oxide layer. The protective spinel-oxide layer is most beneficially formed with chromium present in the metal. It has been demonstrated that the formation of the spinel-oxide layer at the metal surface is a function of the pre-treat temperature, sulfur and acid concentrations, and the availability of chromium in the metal. High sulfur concentration and high pre-treat temperatures can promote the formation of iron sulfide at the metal surface in addition to the formation of the spinel-oxide layer. When both iron sulfide and spinel layers are present, it is difficult to allocate the corrosion protection provided from each. Likewise, since the oxygen source is from the naphthenic acid, either its decomposition or the metal naphthenate, the acid must be available in sufficient quantity. Based on the data herein, the preferred embodiment for forming a protective oxide layer is for a naphthenic acid concentration of 0.5-5.0 mgKOH/g and for a maximum sulfur concentration of 4 percent weight for chrome steel. In addition, the pretreatment time is approximately 24 hours in the temperature range of 250-375° C. It should be clear to one skilled in the art that these ranges can be extended for other metallurgies, crude fractions, times, and temperatures using the methodology of this invention.

The layer analysis methodology in accordance with the presently disclosed subject matter can be used to identify crude oils and fractions thereof that enhance the formation of a protective layer on the exposed surfaces of the refinery piping and processing units associated therewith. The pre-treatment of the components with a suitable crude oil and crude oil fractions may afford a certain degree of corrosion protection against prolonged exposure to corrosive crude oils and crude oil fractions. The desired piping and units may be filled with the selected crude oil or crude oil fraction to permit pre-treatment of the same at a desired pre-treatment temperature to facilitate the formation of the protective layer and enhance corrosion protection.

It will be apparent to those skilled in the art that various modifications and/or variations may be made without departing from the scope of the presently disclosed subject matter. Thus, it is intended that the presently disclosed subject matter covers the modifications and variations of the methods herein, provided they come within the scope of the appended claims and their equivalents.

What is claimed is:

1. A method for evaluating the degree of corrosion protection provided by a corrosion product layer formed on a metal surface from exposure to a corrosive fluid, comprising:
    selecting a fluid containing naphthenic acid with TAN at least 0.5 mg/gKOH;
    said fluid having a maximum sulfur content of 4% by weight
    pre-treating the metal surface by exposing the metal surface to the fluid for a predetermined time period in the range of 16-48 hours and at a predetermined temperature in the range of 200-440° C. to form a corrosion product layer thereon;
    identifying the corrosion protection potential of the corrosion product layer adjacent to the metal surface by examining the morphology and chemical composition of the corrosion product layer adjacent to the metal surface to confirm the formation of spinel-type oxide layer at the metal surface.

2. The method according to claim 1, wherein the fluid is one of a crude oil and a crude oil fraction.

3. The method according to claim 1, wherein the metal surface is formed from steel.

4. The method according to claim 3, wherein the steel is Cr-enriched steel.

5. The method according to claim 3, wherein the steel is a carbon steel.

6. The method according to claim 1, wherein the predetermined time period is approximately 24 hours.

7. The method according to claim 1, wherein the predetermined temperature is approximately between 250° C. and 375° C.

8. The method according to claim 1, wherein the pre-treating the metal surface is performed at a predetermined pressure.

9. The method according to claim 8, wherein the predetermined pressure is autogenous under test conditions.

10. The method according to claim 1, wherein examining the morphology includes using transmission electron microscopy.

11. The method according to claim 10, wherein examining the chemical composition includes using energy-dispersive x-ray spectroscopy analysis.

12. The method according to claim 10, wherein examining the phase composition includes x-ray diffraction.

13. The method according to claim 1, further comprising: assessing the corrosion protection potential of the layer.

14. The method according to claim 13, wherein assessing the corrosion protection potential comprising:
    measuring pre-treatment weight loss of the metal surface;
    challenging the layer formed on the metal surface by exposing the layer to a known corrosive material;
    measuring the weight loss of the metal surface after challenging the layer; and
    comparing the pre-treatment weight loss and the weight loss after challenging the layer.

* * * * *